(12) United States Patent
De Waal et al.

(10) Patent No.: US 11,203,741 B2
(45) Date of Patent: *Dec. 21, 2021

(54) GLYCEROL FREE ETHANOL PRODUCTION

(71) Applicant: DSM IP ASSETS B.V., Heerlen (NL)

(72) Inventors: Paulus Petrus De Waal, Echt (NL); Ingrid Maria Vugt-Van Lutz, Echt (NL); Jozef Petrus Johannes Schmitz, Echt (NL); Hans Marinus Charles Johannes De Bruijn, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/345,610

(22) Filed: Jun. 11, 2021

(65) Prior Publication Data
US 2021/0317420 A1    Oct. 14, 2021

Related U.S. Application Data

(63) Continuation of application No. 17/204,018, filed on Mar. 17, 2021, which is a continuation of application No. 16/470,387, filed as application No. PCT/EP2017/083249 on Dec. 18, 2017, now Pat. No. 10,982,195.

(30) Foreign Application Priority Data

Dec. 23, 2016  (EP) ..................................... 16206564
Sep. 26, 2017  (EP) ..................................... 17193108

(51) Int. Cl.
| | |
|---|---|
| *C12N 9/00* | (2006.01) |
| *C12P 7/14* | (2006.01) |
| *C12N 9/88* | (2006.01) |
| *C12N 9/12* | (2006.01) |
| *C12N 9/04* | (2006.01) |
| *C12N 9/16* | (2006.01) |
| *C12P 7/06* | (2006.01) |

(52) U.S. Cl.
CPC .............. *C12N 9/0006* (2013.01); *C12N 9/12* (2013.01); *C12N 9/1205* (2013.01); *C12N 9/16* (2013.01); *C12N 9/88* (2013.01); *C12P 7/06* (2013.01); *C12P 7/14* (2013.01); *C12Y 101/01006* (2013.01); *C12Y 101/01008* (2013.01); *C12Y 101/01072* (2013.01); *C12Y 101/05003* (2013.01); *C12Y 207/0103* (2013.01); *C12Y 207/01019* (2013.01); *C12Y 207/01028* (2013.01); *C12Y 207/01029* (2013.01); *C12Y 301/03021* (2013.01); *C12Y 401/01039* (2013.01); *Y02E 50/10* (2013.01)

(58) Field of Classification Search
None
See application file for complete search history.

(56) References Cited

U.S. PATENT DOCUMENTS

| | | |
|---|---|---|
| 2016/0208291 A1 | 7/2016 | Klaassen et al. |
| 2019/0330664 A1 | 10/2019 | Klaassen et al. |

FOREIGN PATENT DOCUMENTS

| | | | |
|---|---|---|---|
| WO | 2008028019 A1 | | 3/2008 |
| WO | 2014129898 A2 | | 8/2014 |
| WO | 2015028582 A2 | | 3/2015 |
| WO | 2015028583 A2 | | 3/2015 |
| WO | 2016008819 A1 | | 1/2016 |
| WO | WO 2016097202 | * | 6/2016 |

OTHER PUBLICATIONS

J. Norbeck et al: Metabolic and Regulatory Changes Associated with Growth of *Saccharomyces cerevisiae* in 1.4 M NaCl: Evidence for Osmotic Induction of Glycerol Dissimilation via the Dihydroxyacetone Pathway, Journal of Biological Chemistry, vol. 272, No. 9, 28 (Feb. 28, 1997), pp. 5544-5554.
Victor Guadalupe-Medina et al: "Carbon dioxide fixation by Calvin-Cycle enzymes improves ethanol yield in yeast", Biotechnology for Biofuels, Biomed Central Ltd, GB, vol. 6, No. I, 29 (Aug. 29, 2013), p. 125.
Klaassen P, Hartman, "Zygosaccharomyces rouxii glycerol transporter protein, SEQ 31" WWA: (Apr. 23, 2010). Database accession No. BBV22936. Entire document.
Klaassen P, Hartman "Danio rerio glycerol transporter protein, SEQ 29" WWA: (Apr. 23, 2015). Database accession No. BBV22934. Entire document.
International Search Report of International Patent Application No. PCT/EP2017/083249 dated Apr. 9, 2018.

* cited by examiner

*Primary Examiner* — Suzanne M Noakes
(74) *Attorney, Agent, or Firm* — McBee Moore & Vanik IP, LLC; Susan McBee; Chester Moore

(57) ABSTRACT

The invention relates to a recombinant cell, preferably a yeast cell comprising: a) one or more heterologous genes encoding a glycerol dehydrogenase activity; b) one or more genes encoding a dihydroxyacetone kinase (E.C. 2.7.1.28 and/or E.C. 2.7.1.29); c) one or more heterologous genes encoding a ribulose-1,5-biphosphate carboxylase oxygenase (EC 4.1.1.39, RuBisCO); and d) one or more heterologous genes encoding a phosphoribulokinase (EC 2.7.1.19, PRK); and optionally e) one or more heterologous genes encoding for a glycerol transporter, wherein the recombinant yeast comprises overexpression of one or more PPP-genes. This cell can be used for the production of ethanol and advantageously produces little or no glycerol.

20 Claims, 3 Drawing Sheets

Specification includes a Sequence Listing.

SEQUENCE LISTING

<160> NUMBER OF SEQ ID NOS: 68

<210> SEQ ID NO 1
<211> LENGTH: 2013
<212> TYPE: DNA
<213> ORGANISM: Artificial sequence
<220> FEATURE:
<223> OTHER INFORMATION: Standard subcloning vector with cassette ENO1p-Ec_gldA-CYC1t

<400> SEQUENCE: 1

```
gtgcccgcgg aaccgccaga tattcattac ttgacgcaaa agcgtttgaa ataatgacga      60
aaaagaagga agaaaaaaaa agaaaaatac cgcttctagg cgggttatct actgatccga     120
gcttccacta ggatagcacc caaacacctg catatttgga cgacctttac ttacaccacc     180
aaaaaccact ttcgcctctc ccgcccctga taacgtccac taattgagcg attacctgag     240
cggtcctctt ttgtttgcag catgagactt gcatactgca aatcgtaagt agcaacgtgt     300
caaggtcaaa actgtatgga aaccttgtca cctcacttaa ttctagctag cctaccctgc     360
aagtcaagag gtgtccgtga ttcctagcca cctcaaggta tgcctctccc cggaaactgt     420
ggccttttct ggcacacatg atctccacga tttcaacata taaatagctt ttgataatgg     480
caatattaat caaatttatt ttacttcttt cttgtaacat ctctcttgta atcccttatt     540
ccttctagct atttttcata aaaaaccaag caactgctta tcaacacaca aacactaaat     600
caaaatggac agaatcatcc aatctccagg taagtacatc caaggtgctg atgttatcaa     660
cagattaggt gaatacttga agccattggc tgaaagatgg ttagtcgtcg gtgacaaatt     720
cgttttgggt ttcgctcaat ccaccgtcga aaagtctttc aaggatgctg gtttggttgt     780
tgaaatcgct ccattcggtg gtgaatgttc tcaaaatgaa attgaccgtt tgagaggtat     840
tgctgaaact gctcaatgtg gtgccatctt gggtattggt ggtggtaaga ctttggacac     900
tgccaaggct ttgccccact tcatgggtgt tccagttgcc attgctccaa ccattgcttc     960
taccgatgct ccatgttctg ctttgtccgt tatctacacc gacgaaggtg aatttgaccg    1020
ttacttgttg ttgccaaaca acccaaacat ggtcattgtc gacaccaaga tcgttgccgg    1080
tgctccagcc agattattgg ctgccggtat cggtgatgct ttggctacct ggttcgaagc    1140
cagagcttgt tccagatctg gtgctactac catggccggt ggtaaatgta tcaagctgc    1200
tttagctttg gctgaattgt gttacaacac tttgttggaa gaaggcgaaa aggctatgtt    1260
ggctgctgaa caacacgttg ttactccagc tttggaaaga gtcattgaag ccaacaccta    1320
cttgtccggt gttggattcg aatctggtgg tttagctgcc gctcatgccg tccacaacgg    1380
```

| | |
|---|---|
| tttgactgcc atcccagatg ctcaccacta ctaccacggt gaaaaggttg ctttcggtac | 1440 |
| tttgactcaa ttagtcttgg aaaacgctcc agtcgaagaa atcgaaaccg ttgctgctct | 1500 |
| atcccacgct gtcggtttgc ctatcacttt ggctcaattg gacatcaagg aagatgtccc | 1560 |
| agctaagatg agaattgttg ctgaagctgc ttgtgctgaa ggtgaaacca ttcacaacat | 1620 |
| gccaggtggt gccaccccag accaagtcta cgctgctttg ttggttgctg accaatacgg | 1680 |
| tcaaagattc ttgcaagaat gggagtaaaa caggccccct ttcctttgtc gatatcatgt | 1740 |
| aattagttat gtcacgctta cattcacgcc ctccccccac atccgctcta accgaaaagg | 1800 |
| aaggagttag acaacctgaa gtctaggtcc ctatttattt ttttatagtt atgttagtat | 1860 |
| taagaacgtt atttatattt caaatttttc tttttttcct gtacaaacgc gtgtacgcat | 1920 |
| gtaacattat actgaaaacc ttgcttgaga aggttttggg acgctcgaag ctttaatttt | 1980 |
| gcaagcttcg cagtttacac tctcatcgtc ctc | 2013 |

<210> SEQ ID NO 2
<211> LENGTH: 2664
<212> TYPE: DNA
<213> ORGANISM: Artificial sequence
<220> FEATURE:
<223> OTHER INFORMATION: Standard subcloning vector with cassette
      TPI1p-Sc_DAK1-ENO1t

<400> SEQUENCE: 2

| | |
|---|---|
| gtgcgacacc taactacata gtgtttaaag attacggata tttaacttac ttagaataat | 60 |
| gccattttt tgagttataa taatcctacg ttagtgtgag cgggatttaa actgtgagga | 120 |
| ccttaataca ttcagacact tctgcggtat caccctactt attcccttcg agattatatc | 180 |
| taggaaccca tcaggttggt ggaagattac ccgttctaag acttttcagc ttcctctatt | 240 |
| gatgttacac ctggacaccc cttttctggc atccagtttt taatcttcag tggcatgtga | 300 |
| gattctccga aattaattaa agcaatcaca caattctctc ggataccacc tcggttgaaa | 360 |
| ctgacaggtg gtttgttacg catgctaatg caaaggagcc tatataccttt ggctcggct | 420 |
| gctgtaacag ggaatataaa gggcagcata atttaggagt ttagtgaact tgcaacattt | 480 |
| actatttttcc cttcttacgt aaatattttt ctttttaatt ctaaatcaat cttttttcaat | 540 |
| tttttgtttg tattctttttc ttgcttaaat ctataactac aaaaaacaca tacataaact | 600 |
| aaaaatgtcc gctaaatctt tcgaagttac cgacccagtc aactcttctt tgaagggttt | 660 |
| tgctttggcc aacccatcca ttactttggt cccagaagaa aagatcttat tcagaaagac | 720 |
| tgactctgac aaaattgctt tgatctccgg tggtggttcc ggtcacgaac caacccacgc | 780 |
| tggtttcatc ggtaagggta tgttgtccgg tgctgtcgtt ggtgaaatct ttgcttctcc | 840 |
| atccaccaag caaatcttga atgctatcag attagtcaac gaaaacgctt ctggtgtctt | 900 |
| gttgattgtc aagaactaca ctggtgacgt cttgcatttc ggtttatctg ctgaaagagc | 960 |
| tagagctttg ggtattaact gtagagttgc cgtcatcggt gacgatgttg ctgtcggtcg | 1020 |
| tgaaaagggt ggtatggttg gtagacgtgc tttggctggt actgtcttgg ttcacaagat | 1080 |
| tgttggtgct ttcgctgaag aatactcctc caagtacggt ttagatggta ctgctaaggt | 1140 |
| tgccaagatc atcaacgaca acttggttac catcggttct ctttggacc actgtaaggt | 1200 |
| tccaggtaga aagttcgaat ctgaattgaa cgaaaagcaa atggaattgg gtatgggtat | 1260 |
| ccacaacgaa ccaggtgtta aggtcttgga cccaattcca tccactgaag atttgatttc | 1320 |
| caaatacatg ttgccaaagt tgctagaccc aaacgacaag gacagagctt tcgttaagtt | 1380 |

```
cgatgaagat gacgaagttg ttttgttggt caacaacttg ggtggtgttt ctaacttcgt    1440
catctcttct attacctcca agaccaccga tttcttaaag gaaaactaca acatcactcc    1500
agtccaaacc attgccggta ctttgatgac ctctttcaac ggtaacggtt tctccatcac    1560
cttgttgaat gccaccaaag ctaccaaggc tttgcaatct gatttcgaag aaatcaaatc    1620
cgtcttagat ttgttgaacg ccttcaccaa cgccccaggt tggccaattg ctgacttcga    1680
aaagacctct gctccatctg ttaacgatga cttgttgcac aacgaagtta ctgccaaggc    1740
cgtcggtact tacgatttcg acaaattcgc tgaatggatg aagtctggtg ctgaacaagt    1800
catcaaatct gaaccacaca tcactgaatt ggacaaccaa gttggtgatg gtgactgtgg    1860
ttacactttg gttgctggtg tcaagggtat cactgaaaac ttggacaaat tgtccaagga    1920
ctctttgtct caagctgttg ctcaaatttc tgatttcatt gaaggttcca tgggtggtac    1980
ttctggtggt ttgtactcca tcttgttgtc tggtttctcc cacggtttga tccaagtttg    2040
taagtccaag gatgaacctg tcaccaagga aattgttgcc aagtctctag gtattgcttt    2100
ggacacttta tacaagtaca ccaaggccag aaagggttct tccaccatga tcgatgcttt    2160
ggaaccattt gtcaaggaat tcactgcttc taaggacttc aacaaggctg ttaaggctgc    2220
tgaagaaggt gccaagtcca ctgctacttt cgaagctaag ttcggtagag cttcttacgt    2280
tggtgactct tctcaagttg aagatccagg tgctgttggt ttatgtgaat tcttgaaggg    2340
tgtccaatct gcgcttttaa agcttttgat taagccttct agtccaaaaa acacgttttt    2400
ttgtcattta tttcattttc ttagaatagt ttagtttatt cattttatag tcacgaatgt    2460
tttatgattc tatatagggt tgcaaacaag cattttcat tttatgttaa acaatttca     2520 ggtttacctt ttattctgct tgtggtgacg cgtgtatccg cccgctcttt tggtcaccca    2580
tgtatttaat tgcataaata attcttaaaa gtggagctag tctatttcta tttacatacc    2640
tctcatttct catttcctcc cctc                                            2664
```

<210> SEQ ID NO 3
<211> LENGTH: 1778
<212> TYPE: DNA
<213> ORGANISM: Artificial sequence
<220> FEATURE:
<223> OTHER INFORMATION: Standard subcloning vector with cassette
      ADH1p-Dr_T3-TEF2t

<400> SEQUENCE: 3

```
ggagatatac aatagaacag ataccagaca agacataatg ggctaaacaa gactacacca      60
attacactgc ctcattgatg gtggtacata acgaactaat actgtagccc tagacttgat     120
agccatcatc atatcgaagt ttcactaccc ttttccatt tgccatctat tgaagtaata      180
ataggcgcat gcaacttctt ttcttttttt ttcttttctc tctccccgt tgttgtctca      240 ccatatccgc aatgacaaaa aaatgatgga agacactaaa ggaaaaaatt aacgacaaag     300
acagcaccaa cagatgtcgt tgttccagag ctgatgaggg gtatctcgaa gcacgcgaaa     360 cttttttcctt ccttcattca cgcacactac tctctaatga gcaacggtat acggccttcc    420
ttccagttac ttgaatttga ataaaaaaaa agtttgctgt cttgctatca agtataaata    480
gacctgcaat tattaatctt tgtttcctc gtcattgttc tcgttccctt tcttccttgt    540
ttctttttct gcacaatatt tcaagctata ccaagcatac aatcaactat ctcatataca    600
aatggaatac ttgaaaaaca tcagaaactt gagaggtcgt gtgtcttga aagagatat     660 catcagagaa ttcttggctg aattgttggg tactttcgtc ttgatcttat tcggttgtgg    720
```

```
ttccgttgct caaactgttt tgtccagaga agctaagggt caattattga ccattcactt      780
cggtttcact ttaggtgtca tgttggctgt ctacatggct ggtggtgttt ctggtggtca      840
cgttaaccca gctgtctctt tggccatggt tgttttgaga aagttgccat tgaagaaatt      900
cccagtctac gttttggctc aattcttagg tgctttcttc ggttcttgtg ccgtctactg      960
tttgtactac gatgctttca ccgaatttgc taacggtgaa ttggctgtca ccggtccaaa     1020
tgtcactgct ggtatctttg cttcttaccc aagagaaggt ttatctctat tgaacggttt     1080
cattgaccaa gtcattggtg ccggtgcttt ggttttgtgt atcttggccg ttgttgacaa     1140
gaagaacatt ggtgctccaa agggtatgga acctttgttg gttggtctat ccatcttggc     1200
catcggtgtt tccatggctt tgaactgtgg ttacccaatc aacccagctc gtgacttggg     1260
tccaagatta ttcaccgcca ttgctggttg gggtttgacc gtcttttctg ctggtaacgg     1320
ttggtggtgg gttccagttg tcggtccaat ggtcggtggt gttgtcggtg ctgccatcta     1380
cttcttgatg attgaaatgc accacccaga aaacgacaag aacttggaag atgcaactc      1440 tttgaaggac aaatacgaat tgaacactgt taactaaaga gtaataatta ttgcttccat     1500
ataatatttt tatataccte ttattttat gtattagtta attaagtatt tttatctatc      1560
tgcttatcat tttcttttca tagggggg gttggtgttt tcttgcccat cagattgatg       1620
tcctccaact cggcactatt ttacaaaggg ttttttgta agagaaggag aagacagata      1680
ctaaaccata cgttactcga aacaaaaaaa aaaaaatgg aaaaagctgc tatcaacaaa      1740
agacggcctc atcaaaccta agaaaccat gtcagcgt                              1778

<210> SEQ ID NO 4
<211> LENGTH: 2684
<212> TYPE: DNA
<213> ORGANISM: Artificial sequence
<220> FEATURE:
<223> OTHER INFORMATION: Standard subcloning vector with cassette
      PRE3p-Zr_T5-TEF2t

<400> SEQUENCE: 4
gtgccaaaca ttaatttgtt ctgcatactt tgaacctttc agaaaataaa aaacattacg      60
cgcatactta ccctgctcgc gaagaagagt aacactaacg cattctatgg gcaattgaag     120
acagtattca gtacaagaca tagtccgttt ccttgagtca attcctatag cattatgaac     180
tagccgcctt taagagtgcc aagctgttca acaccgatca tttttgatga tttggcgttt     240
ttgttatatt gatagatttc ttttgaattt tgtcattttc acttttccac tcgcaacgga     300
atccggtggc aaaaaaggga aaagcattga aatgcaatct taacagtat tttaaacaag     360 ttgcgacacg gtgtacaatt acgataagaa ttgctacttc aaagtacaca cagaaagtta     420
acatgaatgg aattcaagtg gacatcaatc gtttgaaaaa gggcgaagtc agtttaggta     480
cctcaatgta tgtatataag aattttttcct cccactttat tgtttctaaa agttcaatga     540
agtaaagtct caattggcct tattactaac taataggtat cttataatca cctaataaaa     600
tagaatgggt aagagaactc aaggtttcat ggactacgtt ttctccagaa cttctactgc     660
tggtttgaaa ggtgccagat tgagatacac tgctgctgcc gttgctgtta tcggtttcgc     720
tttattcggt tacgaccaag gtttgatgtc tggtttgatt accggtgacc aattcaacaa     780
ggaattccct ccaaccaaat ctaacggtga caacgacaga tacgcctccg tcatccaagg     840
tgctgtcact gcttgttacg aaattggttg tttcttcggt tctttgttcg tcttattctt     900
tggtgatgcc atcggtagaa agccattaat cattttcggt gccatcatcg tcatcattgg     960
```

```
tactgttatc tccactgctc cattccacca cgcttggggt ttgggtcaat ttgttgtcgg    1020
tagagttatc actggtgtcg gtactggttt caacacttcc accatcccag tctggcaatc    1080
tgaaatgacc aagccaaaca tcagaggtgc tatgattaac ttggatggtt ccgtcattgc    1140
tttcggtact atgattgctt actggttgga tttcggtttc tctttcatca actcttctgt    1200
tcaatggaga ttcccagttt ccgttcaaat catctttgct ttggtcttat tgttcggtat    1260
tgtcagaatg ccagaatctc caagatggtt gatggccaag aagcgtccag ctgaagccag    1320
atacgttttg gcttgtttga atgacttgcc agaaaacgac gatgccatct tggccgaaat    1380
gacttctttg cacgaagctg tcaacagatc ttctaaccaa aagtctcaaa tgaaatcttt    1440
gttctccatg ggtaagcaac aaaacttctc cagagctttg attgcttcct ctacccaatt    1500
cttccaacaa ttcaccggtt gtaatgctgc catctactac tccactgttt tgttccaaac    1560
caccgttcaa ttagatagat tgttggctat gatcttgggt ggtgtctttg ctaccgttta    1620
caccttgtcc actttgccat cttttctact ggttgaaaag gttggtcgtc gtaagatgtt    1680
cttcttcggt gctttaggtc aaggtatttc tttcattatt acctttgctt gtttggtcaa    1740
cccaaccaag caaaacgcta agggtgctgc tgtcggttta tacttgttca tcatctgttt    1800
cggtttggct atcttggaat tgccatggat ctacccacca gaaattgctt ccatgagagt    1860
cagagctgct accaacgcta tgtccacctg taccaactgg gttaccaact ttgccgttgt    1920
catgttcacc ccagtctttta tccaaaactt ctcaatgggt tgttacttgt tcttcgctgt    1980
catgaacttc atctacttgc ctgttatctt cttcttctac ccagaaactg ccggtcgttc    2040
tttggaagaa atcgatatta ttttcgctaa ggctcatgtt gacggtactc taccatggat    2100
ggttgctcac agattaccaa agttgtccat gactgaagtc gaagattact ctcaatcttt    2160
gggtttgcac gacgatgaaa cgaaaaagga agaatacgac gaaaagaag ctgaagctaa    2220 cgctgccttg ttccaagttg aaacctcttc caagtctcca tcctccaaca gaaaggatga    2280
cgacgctcca attgaacaca acgaagttca agaatctaac gacaactcct ctaactcttc    2340
taacgttgaa gctccaattc cagttcacca caacgaccca taaagagtaa taattattgc    2400
ttccatataa tatttttata tacctcttat ttttatgtat tagttaatta agtattttta    2460
tctatctgct tatcattttc ttttcatata gggggggttg gtgttttctt gcccatcaga    2520
ttgatgtcct ccaactcggc actatttttac aaagggtttt tttgtaagag aaggagaaga    2580
cagatactaa accatacgtt actcgaaaca aaaaaaaaa aaatggaaaa agctgctatc    2640
aacaaaagac ggcctcatca aacctaaaga aaccatgtca gcgt                    2684
```

<210> SEQ ID NO 5
<211> LENGTH: 6167
<212> TYPE: DNA
<213> ORGANISM: Artificial sequence
<220> FEATURE:
<223> OTHER INFORMATION: hphMX-bearing shuttle vector based on pRS305

<400> SEQUENCE: 5

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatcga ctacgtcgta aggccgtttc tgacagagta aaattcttga gggaactttc    240
accattatgg gaaatggttc aagaaggtat tgacttaaac tccatcaaat ggtcaggtca    300
ttgagtgttt tttatttgtt gtattttttt tttttttagag aaaatcctcc aatatcaaat    360
```

```
taggaatcgt agtttcatga ttttctgtta cacctaactt tttgtgtggt gccctcctcc    420
ttgtcaatat taatgttaaa gtgcaattct ttttccttat cacgttgagc cattagtatc    480
aatttgctta cctgtattcc tttactatcc tcctttttct ccttcttgat aaatgtatgt    540
agattgcgta tatagtttcg tctaccctat gaacatattc cattttgtaa tttcgtgtcg    600
tttctattat gaatttcatt tataaagttt atgtacacct aggatccgtc gacactggat    660
ggcggcgtta gtatcgaatc gacagcagta tagcgaccag cattcacata cgattgacgc    720
atgatattac tttctgcgca cttaacttcg catctgggca gatgatgtcg aggcgaaaaa    780
aaatataaat cacgctaaca tttgattaaa atagaacaac tacaatataa aaaaactata    840
caaatgacaa gttcttgaaa acaagaatct ttttattgtc agtactgatt attcctttgc    900
cctcggacga gtgctgggc gtcggtttcc actatcggcg agtacttcta cacagccatc    960
ggtccagacg gccgcgcttc tgcgggcgat tgtgtacgc ccgacagtcc cggctccgga   1020
tcggacgatt gcgtcgcatc gaccctgcgc ccaagctgca tcatcgaaat tgccgtcaac   1080
caagctctga tagagttggt caagaccaat gcggagcata tacgcccgga gccgcggcga   1140
tcctgcaagc tccggatgcc tccgctcgaa gtagcgcgtc tgctgctcca tacaagccaa   1200
ccacggcctc cagaagaaga tgttggcgac ctcgtattgg gaatccccga acatcgcctc   1260
gctccagtca atgaccgctg ttatgcggcc attgtccgtc aggacattgt tggagccgaa   1320
atccgcgtgc acgaggtgcc ggacttcggg gcagtcctcg gcccaaagca tcagctcatc   1380
gagagcctgc gcgacggacg cactgacggt gtcgtccatc acagtttgcc agtgatacac   1440
atggggatca gcaatcgcgc atatgaaatc acgccatgta gtgtattgac cgattccttg   1500
cggtccgaat gggccgaacc cgctcgtctg gctaagatcg gccgcagcga tcgcatccat   1560
ggcctccgcg accggctgca gaacagcggg cagttcggtt tcaggcaggt cttgcaacgt   1620
gacaccctgt gcacggcggg agatgcaata ggtcaggctc tcgctgaatt ccccaatgtc   1680
aagcacttcc ggaatcggga gcgcggccga tgcaaagtgc cgataaacat aacgatcttt   1740
gtagaaacca tcggcgcagc tatttacccg caggacatat ccacgccctc ctacatcgaa   1800
gctgaaagca cgagattctt cgccctccga gagctgcatc aggtcggaga cgctgtcgaa   1860
cttttcgatc agaaacttct cgacagacgt cgcggtgagt tcaggctttt tacccatggt   1920
tgtttatgtt cggatgtgat gtgagaactg tatcctagca agattttaaa aggaagtata   1980
tgaaagaaga acctcagtgg caaatcctaa cctttatat ttctctacag gggcgcggcg   2040
tgggacaat tcacgcgtct gtgagggag cgtttccctg ctcgcaggtc tgcagcgagg   2100
agccgtaatt tttgcttcgc gccgtgcggc catcaaaatg tatggatgca aatgattata   2160
catgggatg tatgggctaa atgtacgggc gacagtcaca tcatgcccct gagctgcgca   2220
cgtcaagact gtcaaggagg gtattctggg cctccatgtc gctggccggg tgaccggcg   2280
gggacgaggc cttaagttcg aacgtacgag ctccggcatt gcgaataccg ctttccacaa   2340
acattgctca aaagtatctc tttgctatat atctctgtgc tatatcccta taacctac    2400
ccatccacct ttcgctcctt gaacttgcat ctaaactcga cctctacatt ttttatgttt   2460
atctctagta ttactcttta gacaaaaaaa ttgtagtaag aactattcat agagtgaatc   2520
gaaaacaata cgaaaatgta aacatttcct atacgtagta tatagagaca aaatagaaga   2580
aaccgttcat aattttctga ccaatgaaga atcatcaacg ctatcacttt ctgttcacaa   2640
agtatgcgca atccacatcg gtatagaata taatcgggga tgcctttatc ttgaaaaaat   2700
gcacccgcag cttcgctagt aatcagtaaa cgcgggaagt ggagtcaggc tttttttatg   2760
```

```
gaagagaaaa tagacaccaa agtagccttc ttctaacctt aacggaccta cagtgcaaaa    2820
agttatcaag agactgcatt atagagcgca caaaggagaa aaaaagtaat ctaagatgct    2880
ttgttagaaa aatagcgctc tcgggatgca ttttttgtaga acaaaaaaga agtatagatt   2940
ctttgttggt aaaatagcgc tctcgcgttg catttctgtt ctgtaaaaat gcagctcaga    3000
ttctttgttt gaaaaattag cgctctcgcg ttgcattttt gttttacaaa aatgaagcac    3060
agattcttcg ttggtaaaat agcgcttccg cgttgcattt ctgttctgta aaaatgcagc    3120
tcagattctt tgtttgaaaa attagcgctc tcgcgttgca ttttttgttct acaaaatgaa   3180 gcacagatgc ttcgttaaca aagatatgct attgaagtgc aagatggaaa cgcagaaaat    3240
gaaccgggga tgcgacgtgc aagattacct atgcaataga tgcaatagtt tctccaggaa    3300
ccgaaataca tacattgtct tccgtaaagc gctagactat atattattat acaggttcaa    3360
atatactatc tgtttcaggg aaaactccca ggttcggatg ttcaaaattc aatgatgggt    3420
aacaagtacg atcgtaaatc tgtaaaacag tttgtcggat attaggctgt atctcctcaa    3480
agcgtattcg aatatcattg agaagctgca gcgtcacatc ggataataat gatggcagcc    3540
attgtagaag tgccttttgc atttctagtc tctttctcgg tctagctagt tttactacat    3600
cgcgaagata gaatcttaga tcacactgcc tttgctgagc tggatcaata gagtaacaaa    3660
agagtggtaa ggcctcgtta aaggacaagg acctgagcgg aagtgtatcg tacagtagac    3720
ggagtatact aggtatagtc tatagtccgt ggaattaatt ctcatgtttg acagcttatc    3780
atcgataatc cggagctagc atgcggccgc tctagaacta gtggatcccc cgggctgcag    3840
gaattcgata tcaagcttat cgataccgtc gacctcgagg gggggcccgg tacccagctt    3900
ttgttccctt tagtgagggt taattccgag cttggcgtaa tcatggtcat agctgtttcc    3960
tgtgtgaaat tgttatccgc tcacaattcc acacaacata ggagccggaa gcataaagtg    4020
taaagcctgg ggtgcctaat gagtgaggta actcacatta attgcgttgc gctcactgcc    4080 cgcttccag tcgggaaacc tgtcgtgcca gctgcattaa tgaatcggcc aacgcgcggg     4140
gagaggcggt ttgcgtattg ggcgctcttc cgcttcctcg ctcactgact cgctgcgctc    4200 ggtcgttcg ctgcggcgag cggtatcagc tcactcaaag gcggtaatac ggttatccac     4260
agaatcaggg gataacgcag gaaagaacat gtgagcaaaa ggccagcaaa aggccaggaa    4320
ccgtaaaaag gccgcgttgc tggcgttttt ccataggctc ggcccccctg acgagcatca    4380
caaaaatcga cgctcaagtc agaggtggcg aaacccgaca ggactataaa gataccaggc    4440
gttcccccct ggaagctccc tcgtgcgctc tcctgttccg accctgccgc ttaccggata    4500
cctgtccgcc tttctccctt cgggaagcgt ggcgctttct caatgctcac gctgtaggta    4560
tctcagttcg gtgtaggtcg ttcgctccaa gctgggctgt gtgcacgaac cccccgttca    4620
gcccgaccgc tgcgccttat ccggtaacta tcgtcttgag tccaacccgg taagacacga    4680
cttatcgcca ctggcagcag ccactggtaa caggattagc agagcgaggt atgtaggcgg    4740
tgctacagag ttcttgaagt ggtggcctaa ctacggctac actagaagga cagtatttgg    4800
tatctgcgct ctgctgaagc cagttacctt cggaaaaaga gttggtagct cttgatccgg    4860
caaacaaacc accgctggta gcggtggttt ttttgtttgc aagcagcaga ttacgcgcag    4920
aaaaaaagga tctcaagaag atcctttgat cttttctacg gggtctgacg ctcagtggaa    4980
cgaaaactca cgttaaggga ttttggtcat gagattatca aaaaggatct tcacctagat    5040
ccttttaaat taaaaatgaa gttttaaatc aatctaaagt atatatgagt aaacttggtc    5100
```

```
tgacagttac caatgcttaa tcagtgaggc acctatctca gcgatctgtc tatttcgttc    5160
atccatagtt gcctgactgc ccgtcgtgta gataactacg atacgggagg gcttaccatc    5220
tggccccagt gctgcaatga taccgcgaga cccacgctca ccggctccag atttatcagc    5280
aataaaccag ccagccggaa gggccgagcg cagaagtggt cctgcaactt tatccgcctc    5340
catccagtct attaattgtt gccgggaagc tagagtaagt agttcgccag ttaatagttt    5400
gcgcaacgtt gttgccattg ctacaggcat cgtggtgtca cgctcgtcgt ttggtatggc    5460
ttcattcagc tccggttccc aacgatcaag gcgagttaca tgatccccca tgttgtgaaa    5520
aaaagcggtt agctccttcg gtcctccgat cgttgtcaga agtaagttgg ccgcagtgtt    5580
atcactcatg gttatggcag cactgcataa ttctcttact gtcatgccat ccgtaagatg    5640
cttttctgtg actggtgagt actcaaccaa gtcattctga atagtgta tgcggcgacc     5700 gagttgctct tgcccggcgt caatacggga taataccgcg ccacatagca gaactttaaa    5760
agtgctcatc attggaaaac gttcttcggg gcgaaaactc tcaaggatct taccgctgtt    5820
gagatccagt tcgatgtaac ccactcgtgc acccaactga tcttcagcat cttttacttt    5880
caccagcgtt tctgggtgag caaaaacagg aaggcaaaat gccgcaaaaa agggaataag    5940
ggcgacacgg aaatgttgaa tactcatact cttccttttt caatattatt gaagcattta    6000
tcagggttat tgtctcatga gcggatacat atttgaatgt atttagaaaa ataaacaaat    6060
aggggttccg cgcacatttc cccgaaaagt gccacctgac gtctaagaaa ccattattat    6120
catgacatta acctataaaa ataggcgtat cacgaggccc tttcgtc                  6167

<210> SEQ ID NO 6
<211> LENGTH: 486
<212> TYPE: DNA
<213> ORGANISM: Artificial sequence
<220> FEATURE:
<223> OTHER INFORMATION: gBLOCK bearing sequence of SNR52p-gRNA.INT1-
      SUP4t

<400> SEQUENCE: 6
ctgcagcccg ggggatccac tagttctaga gcggccgcca ccgcccgcgg tctttgaaaa      60
gataatgtat gattatgctt tcactcatat ttatacagaa acttgatgtt ttctttcgag     120
tatatacaag gtgattacat gtacgtttga agtacaactc tagattttgt agtgccctct    180
tgggctagcg gtaaaggtgc gcatttttc acaccctaca atgttctgtt caaaagattt     240
tggtcaaacg ctgtagaagt gaagttggt gcgcatgttt cggcgttcga aacttctccg     300
cagtgaaaga taaatgatct attagaacca gggaggtccg ttttagagct agaaatagca    360
agttaaaata aggctagtcc gttatcaact tgaaaaagtg gcaccgagtc ggtggtgctt    420 ttttttgtttt ttatgtctcc gcggcaatta accctcacta aagggaacaa agctggagc    480 tccacc                                                               486

<210> SEQ ID NO 7
<211> LENGTH: 291
<212> TYPE: PRT
<213> ORGANISM: Danio rerio
<220> FEATURE:
<221> NAME/KEY: MISC_FEATURE
<222> LOCATION: (1)..(291)
<223> OTHER INFORMATION: Aquaporin 9 (Aqp9)
```

<400> SEQUENCE: 7

```
Met Glu Tyr Leu Glu Asn Ile Arg Asn Leu Arg Gly Arg Cys Val Leu
1               5                   10                  15

Arg Arg Asp Ile Ile Arg Glu Phe Leu Ala Glu Leu Leu Gly Thr Phe
            20                  25                  30

Val Leu Ile Leu Phe Gly Cys Gly Ser Val Ala Gln Thr Val Leu Ser
        35                  40                  45

Arg Glu Ala Lys Gly Gln Leu Leu Thr Ile His Phe Gly Phe Thr Leu
    50                  55                  60

Gly Val Met Leu Ala Val Tyr Met Ala Gly Gly Val Ser Gly Gly His
65                  70                  75                  80

Val Asn Pro Ala Val Ser Leu Ala Met Val Val Leu Arg Lys Leu Pro
                85                  90                  95

Leu Lys Lys Phe Pro Val Tyr Val Leu Ala Gln Phe Leu Gly Ala Phe
            100                 105                 110

Phe Gly Ser Cys Ala Val Tyr Cys Leu Tyr Tyr Asp Ala Phe Thr Glu
        115                 120                 125

Phe Ala Asn Gly Glu Leu Ala Val Thr Gly Pro Asn Val Thr Ala Gly
    130                 135                 140

Ile Phe Ala Ser Tyr Pro Arg Glu Gly Leu Ser Leu Leu Asn Gly Phe
145                 150                 155                 160

Ile Asp Gln Val Ile Gly Ala Gly Ala Leu Val Leu Cys Ile Leu Ala
                165                 170                 175

Val Val Asp Lys Lys Asn Ile Gly Ala Pro Lys Gly Met Glu Pro Leu
            180                 185                 190

Leu Val Gly Leu Ser Ile Leu Ala Ile Gly Val Ser Met Ala Leu Asn
        195                 200                 205

Cys Gly Tyr Pro Ile Asn Pro Ala Arg Asp Leu Gly Pro Arg Leu Phe
    210                 215                 220

Thr Ala Ile Ala Gly Trp Gly Leu Thr Val Phe Ser Ala Gly Asn Gly
225                 230                 235                 240

Trp Trp Trp Val Pro Val Val Gly Pro Met Val Gly Gly Val Val Gly
                245                 250                 255

Ala Ala Ile Tyr Phe Leu Met Ile Glu Met His His Pro Glu Asn Asp
            260                 265                 270

Lys Asn Leu Glu Asp Asp Asn Ser Leu Lys Lys Tyr Glu Leu Asn
        275                 280                 285

Thr Val Asn
    290
```

<210> SEQ ID NO 8
<211> LENGTH: 592
<212> TYPE: PRT
<213> ORGANISM: Zygosaccharomyces rouxii
<220> FEATURE:
<221> NAME/KEY: MISC_FEATURE
<222> LOCATION: (1)..(592)
<223> OTHER INFORMATION: ZYR00E01210p

<400> SEQUENCE: 8

```
Met Gly Lys Arg Thr Gln Gly Phe Met Asp Tyr Val Phe Ser Arg Thr
1               5                   10                  15

Ser Thr Ala Gly Leu Lys Gly Ala Arg Leu Arg Tyr Thr Ala Ala Ala
            20                  25                  30

Val Ala Val Ile Gly Phe Ala Leu Phe Gly Tyr Asp Gln Gly Leu Met
        35                  40                  45
```

-continued

Ser Gly Leu Ile Thr Gly Asp Gln Phe Asn Lys Glu Phe Pro Pro Thr
 50              55                  60

Lys Ser Asn Gly Asp Asn Asp Arg Tyr Ala Ser Val Ile Gln Gly Ala
 65              70                  75                  80

Val Thr Ala Cys Tyr Glu Ile Gly Cys Phe Phe Gly Ser Leu Phe Val
             85                  90                  95

Leu Phe Phe Gly Asp Ala Ile Gly Arg Lys Pro Leu Ile Ile Phe Gly
            100                 105                 110

Ala Ile Val Ile Ile Gly Thr Val Ile Ser Thr Ala Pro Phe His
        115                 120                 125

His Ala Trp Gly Leu Gly Gln Phe Val Val Gly Arg Val Ile Thr Gly
    130                 135                 140

Val Gly Thr Gly Phe Asn Thr Ser Thr Ile Pro Val Trp Gln Ser Glu
145                 150                 155                 160

Met Thr Lys Pro Asn Ile Arg Gly Ala Met Ile Asn Leu Asp Gly Ser
                165                 170                 175

Val Ile Ala Phe Gly Thr Met Ile Ala Tyr Trp Leu Asp Phe Gly Phe
            180                 185                 190

Ser Phe Ile Asn Ser Ser Val Gln Trp Arg Phe Pro Val Ser Val Gln
        195                 200                 205

Ile Ile Phe Ala Leu Val Leu Leu Phe Gly Ile Val Arg Met Pro Glu
210                 215                 220

Ser Pro Arg Trp Leu Met Ala Lys Lys Arg Pro Ala Glu Ala Arg Tyr
225                 230                 235                 240

Val Leu Ala Cys Leu Asn Asp Leu Pro Glu Asn Asp Asp Ala Ile Leu
                245                 250                 255

Ala Glu Met Thr Ser Leu His Glu Ala Val Asn Arg Ser Ser Asn Gln
            260                 265                 270

Lys Ser Gln Met Lys Ser Leu Phe Ser Met Gly Lys Gln Gln Asn Phe
        275                 280                 285

Ser Arg Ala Leu Ile Ala Ser Ser Thr Gln Phe Phe Gln Gln Phe Thr
290                 295                 300

Gly Cys Asn Ala Ala Ile Tyr Tyr Ser Thr Val Leu Phe Gln Thr Thr
305                 310                 315                 320

Val Gln Leu Asp Arg Leu Leu Ala Met Ile Leu Gly Gly Val Phe Ala
                325                 330                 335

Thr Val Tyr Thr Leu Ser Thr Leu Pro Ser Phe Tyr Leu Val Glu Lys
            340                 345                 350

Val Gly Arg Arg Lys Met Phe Phe Phe Gly Ala Leu Gly Gln Gly Ile
        355                 360                 365

Ser Phe Ile Ile Thr Phe Ala Cys Leu Val Asn Pro Thr Lys Gln Asn
370                 375                 380

Ala Lys Gly Ala Ala Val Gly Leu Tyr Leu Phe Ile Ile Cys Phe Gly
385                 390                 395                 400

Leu Ala Ile Leu Glu Leu Pro Trp Ile Tyr Pro Pro Glu Ile Ala Ser
                405                 410                 415

Met Arg Val Arg Ala Ala Thr Asn Ala Met Ser Thr Cys Thr Asn Trp
            420                 425                 430

Val Thr Asn Phe Ala Val Val Met Phe Thr Pro Val Phe Ile Gln Thr
        435                 440                 445

Ser Gln Trp Gly Cys Tyr Leu Phe Phe Ala Val Met Asn Phe Ile Tyr
450                 455                 460

```
Leu Pro Val Ile Phe Phe Tyr Pro Glu Thr Ala Gly Arg Ser Leu
465                 470                 475                 480

Glu Glu Ile Asp Ile Ile Phe Ala Lys Ala His Val Asp Gly Thr Leu
            485                 490                 495

Pro Trp Met Val Ala His Arg Leu Pro Lys Leu Ser Met Thr Glu Val
        500                 505                 510

Glu Asp Tyr Ser Gln Ser Leu Gly Leu His Asp Asp Glu Asn Glu Lys
    515                 520                 525

Glu Glu Tyr Asp Glu Lys Gly Ala Glu Ala Asn Ala Ala Leu Phe Gln
530                 535                 540

Val Glu Thr Ser Ser Lys Ser Pro Ser Ser Asn Arg Lys Asp Asp
545                 550                 555                 560

Ala Pro Ile Glu His Asn Glu Val Gln Glu Ser Asn Asp Asn Ser Ser
                565                 570                 575

Asn Ser Ser Asn Val Glu Ala Pro Ile Pro Val His His Asn Asp Pro
            580                 585                 590
```

<210> SEQ ID NO 9
<211> LENGTH: 97
<212> TYPE: PRT
<213> ORGANISM: Escherichia coli
<220> FEATURE:
<221> NAME/KEY: MISC_FEATURE
<222> LOCATION: (1)..(97)
<223> OTHER INFORMATION: groES

<400> SEQUENCE: 9

```
Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Gly Asn Gly Arg Ile
        35                  40                  45

Leu Glu Asn Gly Glu Val Lys Pro Leu Asp Val Lys Val Gly Asp Ile
    50                  55                  60

Val Ile Phe Asn Asp Gly Tyr Gly Val Lys Ser Glu Lys Ile Asp Asn
65                  70                  75                  80

Glu Glu Val Leu Ile Met Ser Glu Ser Asp Ile Leu Ala Ile Val Glu
                85                  90                  95

Ala
```

<210> SEQ ID NO 10
<211> LENGTH: 548
<212> TYPE: PRT
<213> ORGANISM: Escherichia coli
<220> FEATURE:
<221> NAME/KEY: MISC_FEATURE
<222> LOCATION: (1)..(548)
<223> OTHER INFORMATION: groEL

<400> SEQUENCE: 10

```
Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
            20                  25                  30

Pro Lys Gly Arg Asn Val Val Leu Asp Lys Ser Phe Gly Ala Pro Thr
        35                  40                  45

Ile Thr Lys Asp Gly Val Ser Val Ala Arg Glu Ile Glu Leu Glu Asp
    50                  55                  60
```

-continued

```
Lys Phe Glu Asn Met Gly Ala Gln Met Val Lys Glu Val Ala Ser Lys
 65                  70                  75                  80

Ala Asn Asp Ala Ala Gly Asp Gly Thr Thr Thr Ala Thr Val Leu Ala
                 85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Ala Ala Val
            115                 120                 125

Glu Glu Leu Lys Ala Leu Ser Val Pro Cys Ser Asp Ser Lys Ala Ile
        130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
        195                 200                 205

Glu Thr Gly Ala Val Glu Leu Glu Ser Pro Phe Ile Leu Leu Ala Asp
    210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Leu Val Val Asn Thr Met Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Thr Leu Thr Gly Gly Thr Val Ile Ser Glu Glu
290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
            340                 345                 350

Ile Glu Glu Ala Thr Ser Asp Tyr Asp Arg Glu Lys Leu Gln Glu Arg
        355                 360                 365

Val Ala Lys Leu Ala Gly Gly Val Ala Val Ile Lys Val Gly Ala Ala
    370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Val Ala Ser Lys Leu Ala Asp Leu Arg Gly Gln
            420                 425                 430

Asn Glu Asp Gln Asn Val Gly Ile Lys Val Ala Leu Arg Ala Met Glu
        435                 440                 445

Ala Pro Leu Arg Gln Ile Val Leu Asn Cys Gly Glu Glu Pro Ser Val
    450                 455                 460

Val Ala Asn Thr Val Lys Gly Gly Asp Gly Asn Tyr Gly Tyr Asn Ala
465                 470                 475                 480
```

```
Ala Thr Glu Glu Tyr Gly Asn Met Ile Asp Met Gly Ile Leu Asp Pro
                485                 490                 495

Thr Lys Val Thr Arg Ser Ala Leu Gln Tyr Ala Ala Ser Val Ala Gly
            500                 505                 510

Leu Met Ile Thr Thr Glu Cys Met Val Thr Asp Leu Pro Lys Asn Asp
        515                 520                 525

Ala Ala Asp Leu Gly Ala Ala Gly Gly Met Gly Gly Met Gly Gly Met
    530                 535                 540

Gly Gly Met Met
545

<210> SEQ ID NO 11
<211> LENGTH: 459
<212> TYPE: PRT
<213> ORGANISM: Thiobacillus denitrificans
<220> FEATURE:
<221> NAME/KEY: MISC_FEATURE
<222> LOCATION: (1)..(459)
<223> OTHER INFORMATION: Rubisco large subunit CbbM

<400> SEQUENCE: 11

Met Asp Gln Ser Ala Arg Tyr Ala Asp Leu Ser Leu Lys Glu Glu Asp
1               5                   10                  15

Leu Ile Lys Gly Gly Arg His Ile Leu Val Ala Tyr Lys Met Lys Pro
            20                  25                  30

Lys Ser Gly Tyr Gly Tyr Leu Glu Ala Ala Ala His Phe Ala Ala Glu
        35                  40                  45

Ser Ser Thr Gly Thr Asn Val Glu Val Ser Thr Thr Asp Asp Phe Thr
    50                  55                  60

Lys Gly Val Asp Ala Leu Val Tyr Tyr Ile Asp Glu Ala Ser Glu Asp
65                  70                  75                  80

Met Arg Ile Ala Tyr Pro Leu Glu Leu Phe Asp Arg Asn Val Thr Asp
                85                  90                  95

Gly Arg Phe Met Leu Val Ser Phe Leu Thr Leu Ala Ile Gly Asn Asn
            100                 105                 110

Gln Gly Met Gly Asp Ile Glu His Ala Lys Met Ile Asp Phe Tyr Val
        115                 120                 125

Pro Glu Arg Cys Ile Gln Met Phe Asp Gly Pro Ala Thr Asp Ile Ser
    130                 135                 140

Asn Leu Trp Arg Ile Leu Gly Arg Pro Val Val Asn Gly Gly Tyr Ile
145                 150                 155                 160

Ala Gly Thr Ile Ile Lys Pro Lys Leu Gly Leu Arg Pro Glu Pro Phe
                165                 170                 175

Ala Lys Ala Ala Tyr Gln Phe Trp Leu Gly Gly Asp Phe Ile Lys Asn
            180                 185                 190

Asp Glu Pro Gln Gly Asn Gln Val Phe Cys Pro Leu Lys Lys Val Leu
        195                 200                 205

Pro Leu Val Tyr Asp Ala Met Lys Arg Ala Gln Asp Thr Gly Gln
    210                 215                 220

Ala Lys Leu Phe Ser Met Asn Ile Thr Ala Asp Asp His Tyr Glu Met
225                 230                 235                 240

Cys Ala Arg Ala Asp Tyr Ala Leu Glu Val Phe Gly Pro Asp Ala Asp
                245                 250                 255

Lys Leu Ala Phe Leu Val Asp Gly Tyr Val Gly Gly Pro Gly Met Val
            260                 265                 270
```

```
Thr Thr Ala Arg Arg Gln Tyr Pro Gly Gln Tyr Leu His Tyr His Arg
            275                 280                 285

Ala Gly His Gly Ala Val Thr Ser Pro Ser Ala Lys Arg Gly Tyr Thr
        290                 295                 300

Ala Phe Val Leu Ala Lys Met Ser Arg Leu Gln Gly Ala Ser Gly Ile
305                 310                 315                 320

His Val Gly Thr Met Gly Tyr Gly Lys Met Glu Gly Glu Gly Asp Asp
                325                 330                 335

Lys Ile Ile Ala Tyr Met Ile Glu Arg Asp Glu Cys Gln Gly Pro Val
            340                 345                 350

Tyr Phe Gln Lys Trp Tyr Gly Met Lys Pro Thr Thr Pro Ile Ile Ser
        355                 360                 365

Gly Gly Met Asn Ala Leu Arg Leu Pro Gly Phe Phe Glu Asn Leu Gly
    370                 375                 380

His Gly Asn Val Ile Asn Thr Ala Gly Gly Ser Tyr Gly His Ile
385                 390                 395                 400

Asp Ser Pro Ala Ala Gly Ala Ile Ser Leu Arg Gln Ser Tyr Glu Cys
                405                 410                 415

Trp Lys Gln Gly Ala Asp Pro Ile Glu Phe Ala Lys Glu His Lys Glu
            420                 425                 430

Phe Ala Arg Ala Phe Glu Ser Phe Pro Lys Asp Ala Asp Lys Leu Phe
        435                 440                 445

Pro Gly Trp Arg Glu Lys Leu Gly Val His Ser
    450                 455

<210> SEQ ID NO 12
<211> LENGTH: 352
<212> TYPE: PRT
<213> ORGANISM: Spinacia oleracea
<220> FEATURE:
<221> NAME/KEY: MISC_FEATURE
<222> LOCATION: (1)..(352)
<223> OTHER INFORMATION: Phosphoribulokinase (prk)

<400> SEQUENCE: 12

Met Ser Gln Gln Gln Thr Ile Val Ile Gly Leu Ala Ala Asp Ser Gly
1               5                   10                  15

Cys Gly Lys Ser Thr Phe Met Arg Arg Leu Thr Ser Val Phe Gly Gly
            20                  25                  30

Ala Ala Glu Pro Pro Lys Gly Gly Asn Pro Asp Ser Asn Thr Leu Ile
        35                  40                  45

Ser Asp Thr Thr Thr Val Ile Cys Leu Asp Asp Phe His Ser Leu Asp
    50                  55                  60

Arg Asn Gly Arg Lys Val Glu Lys Val Thr Ala Leu Asp Pro Lys Ala
65                  70                  75                  80

Asn Asp Phe Asp Leu Met Tyr Glu Gln Val Lys Ala Leu Lys Glu Gly
                85                  90                  95

Lys Ala Val Asp Lys Pro Ile Tyr Asn His Val Ser Gly Leu Leu Asp
            100                 105                 110

Pro Pro Glu Leu Ile Gln Pro Pro Lys Ile Leu Val Ile Glu Gly Leu
        115                 120                 125

His Pro Met Tyr Asp Ala Arg Val Arg Glu Leu Leu Asp Phe Ser Ile
    130                 135                 140

Tyr Leu Asp Ile Ser Asn Glu Val Lys Phe Ala Trp Lys Ile Gln Arg
145                 150                 155                 160
```

```
Asp Met Lys Glu Arg Gly His Ser Leu Glu Ser Ile Lys Ala Ser Ile
            165                 170                 175

Glu Ser Arg Lys Pro Asp Phe Asp Ala Tyr Ile Asp Pro Gln Lys Gln
        180                 185                 190

His Ala Asp Val Val Ile Glu Val Leu Pro Thr Glu Leu Ile Pro Asp
    195                 200                 205

Asp Asp Glu Gly Lys Val Leu Arg Val Arg Met Ile Gln Lys Glu Gly
210                 215                 220

Val Lys Phe Phe Asn Pro Val Tyr Leu Phe Asp Gly Ser Thr Ile
225                 230                 235                 240

Ser Trp Ile Pro Cys Gly Arg Lys Leu Thr Cys Ser Tyr Pro Gly Ile
                245                 250                 255

Lys Phe Ser Tyr Gly Pro Asp Thr Phe Tyr Gly Asn Glu Val Thr Val
            260                 265                 270

Val Glu Met Asp Gly Met Phe Asp Arg Leu Asp Glu Leu Ile Tyr Val
        275                 280                 285

Glu Ser His Leu Ser Asn Leu Ser Thr Lys Phe Tyr Gly Glu Val Thr
    290                 295                 300

Gln Gln Met Leu Lys His Gln Asn Phe Pro Gly Ser Asn Asn Gly Thr
305                 310                 315                 320

Gly Phe Phe Gln Thr Ile Ile Gly Leu Lys Ile Arg Asp Leu Phe Glu
                325                 330                 335

Gln Leu Val Ala Ser Arg Ser Thr Ala Thr Ala Thr Ala Ala Lys Ala
            340                 345                 350

<210> SEQ ID NO 13
<211> LENGTH: 367
<212> TYPE: PRT
<213> ORGANISM: Escherichia coli
<220> FEATURE:
<221> NAME/KEY: MISC_FEATURE
<222> LOCATION: (1)..(367)
<223> OTHER INFORMATION: gldA

<400> SEQUENCE: 13

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Ala
145                 150                 155                 160
```

```
Pro Ala Arg Leu Leu Ala Ala Gly Ile Gly Asp Ala Leu Ala Thr Trp
            165                 170                 175

Phe Glu Ala Arg Ala Cys Ser Arg Ser Gly Ala Thr Thr Met Ala Gly
        180                 185                 190

Gly Lys Cys Thr Gln Ala Ala Leu Ala Leu Ala Glu Leu Cys Tyr Asn
    195                 200                 205

Thr Leu Leu Glu Glu Gly Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Leu Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
    275                 280                 285

Pro Val Glu Glu Ile Glu Thr Val Ala Ala Leu Ser His Ala Val Gly
        290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
        355                 360                 365

<210> SEQ ID NO 14
<211> LENGTH: 584
<212> TYPE: PRT
<213> ORGANISM: Saccharomyces cerevisiae
<220> FEATURE:
<221> NAME/KEY: MISC_FEATURE
<222> LOCATION: (1)..(584)
<223> OTHER INFORMATION: DAK1

<400> SEQUENCE: 14

Met Ser Ala Lys Ser Phe Glu Val Thr Asp Pro Val Asn Ser Ser Leu
1               5                   10                  15

Lys Gly Phe Ala Leu Ala Asn Pro Ser Ile Thr Leu Val Pro Glu Glu
            20                  25                  30

Lys Ile Leu Phe Arg Lys Thr Asp Ser Asp Lys Ile Ala Leu Ile Ser
        35                  40                  45

Gly Gly Gly Ser Gly His Glu Pro Thr His Ala Gly Phe Ile Gly Lys
    50                  55                  60

Gly Met Leu Ser Gly Ala Val Val Gly Glu Ile Phe Ala Ser Pro Ser
65                  70                  75                  80

Thr Lys Gln Ile Leu Asn Ala Ile Arg Leu Val Asn Glu Asn Ala Ser
                85                  90                  95

Gly Val Leu Leu Ile Val Lys Asn Tyr Thr Gly Asp Val Leu His Phe
            100                 105                 110

Gly Leu Ser Ala Glu Arg Ala Arg Ala Leu Gly Ile Asn Cys Arg Val
        115                 120                 125

Ala Val Ile Gly Asp Asp Val Ala Val Gly Arg Glu Lys Gly Gly Met
    130                 135                 140
```

```
Val Gly Arg Arg Ala Leu Ala Gly Thr Val Leu Val His Lys Ile Val
145                 150                 155                 160

Gly Ala Phe Ala Glu Glu Tyr Ser Ser Lys Tyr Gly Leu Asp Gly Thr
                165                 170                 175

Ala Lys Val Ala Lys Ile Ile Asn Asp Asn Leu Val Thr Ile Gly Ser
                180                 185                 190

Ser Leu Asp His Cys Lys Val Pro Gly Arg Lys Phe Glu Ser Glu Leu
            195                 200                 205

Asn Glu Lys Gln Met Glu Leu Gly Met Gly Ile His Asn Glu Pro Gly
        210                 215                 220

Val Lys Val Leu Asp Pro Ile Pro Ser Thr Glu Asp Leu Ile Ser Lys
225                 230                 235                 240

Tyr Met Leu Pro Lys Leu Leu Asp Pro Asn Asp Lys Asp Arg Ala Phe
                245                 250                 255

Val Lys Phe Asp Glu Asp Glu Val Val Leu Leu Val Asn Asn Leu
            260                 265                 270

Gly Gly Val Ser Asn Phe Val Ile Ser Ser Ile Thr Ser Lys Thr Thr
            275                 280                 285

Asp Phe Leu Lys Glu Asn Tyr Asn Ile Thr Pro Val Gln Thr Ile Ala
        290                 295                 300

Gly Thr Leu Met Thr Ser Phe Asn Gly Asn Gly Phe Ser Ile Thr Leu
305                 310                 315                 320

Leu Asn Ala Thr Lys Ala Thr Lys Ala Leu Gln Ser Asp Phe Glu Glu
                325                 330                 335

Ile Lys Ser Val Leu Asp Leu Leu Asn Ala Phe Thr Asn Ala Pro Gly
            340                 345                 350

Trp Pro Ile Ala Asp Phe Glu Lys Thr Ser Ala Pro Ser Val Asn Asp
        355                 360                 365

Asp Leu Leu His Asn Glu Val Thr Ala Lys Ala Val Gly Thr Tyr Asp
        370                 375                 380

Phe Asp Lys Phe Ala Glu Trp Met Lys Ser Gly Ala Glu Gln Val Ile
385                 390                 395                 400

Lys Ser Glu Pro His Ile Thr Glu Leu Asp Asn Gln Val Gly Asp Gly
                405                 410                 415

Asp Cys Gly Tyr Thr Leu Val Ala Gly Val Lys Gly Ile Thr Glu Asn
            420                 425                 430

Leu Asp Lys Leu Ser Lys Asp Ser Leu Ser Gln Ala Val Ala Gln Ile
        435                 440                 445

Ser Asp Phe Ile Glu Gly Ser Met Gly Gly Thr Ser Gly Gly Leu Tyr
        450                 455                 460

Ser Ile Leu Leu Ser Gly Phe Ser His Gly Leu Ile Gln Val Cys Lys
465                 470                 475                 480

Ser Lys Asp Glu Pro Val Thr Lys Glu Ile Val Ala Lys Ser Leu Gly
                485                 490                 495

Ile Ala Leu Asp Thr Leu Tyr Lys Tyr Thr Lys Ala Arg Lys Gly Ser
            500                 505                 510

Ser Thr Met Ile Asp Ala Leu Glu Pro Phe Val Lys Glu Phe Thr Ala
        515                 520                 525

Ser Lys Asp Phe Asn Lys Ala Val Lys Ala Glu Glu Gly Ala Lys
        530                 535                 540

Ser Thr Ala Thr Phe Glu Ala Lys Phe Gly Arg Ala Ser Tyr Val Gly
545                 550                 555                 560
```

Asp Ser Ser Gln Val Glu Asp Pro Gly Ala Val Gly Leu Cys Glu Phe
            565                 570                 575

Leu Lys Gly Val Gln Ser Ala Leu
            580

<210> SEQ ID NO 15
<211> LENGTH: 12
<212> TYPE: DNA
<213> ORGANISM: Artificial Sequence
<220> FEATURE:
<223> OTHER INFORMATION: PRK promoter sequence motif
<220> FEATURE:
<221> NAME/KEY: misc_feature
<222> LOCATION: (1)..(3)
<223> OTHER INFORMATION: n can be, independently, a, c, t, or g
<220> FEATURE:
<221> NAME/KEY: misc_feature
<222> LOCATION: (10)..(12)
<223> OTHER INFORMATION: n can be, independently, a, c, t, or g

<400> SEQUENCE: 15
nnnattgttn nn                                                        12

<210> SEQ ID NO 16
<211> LENGTH: 12
<212> TYPE: DNA
<213> ORGANISM: Artificial Sequence
<220> FEATURE:
<223> OTHER INFORMATION: PRK promoter sequence motif

<400> SEQUENCE: 16
aaaaattgtt ga                                                        12

<210> SEQ ID NO 17
<211> LENGTH: 33
<212> TYPE: DNA
<213> ORGANISM: Artificial Sequence
<220> FEATURE:
<223> OTHER INFORMATION: Amino acid sequence of primer for pUDR119 and
      pUDR164 construction

<400> SEQUENCE: 17
gttttagagc tagaaatagc aagttaaaat aag                                 33

<210> SEQ ID NO 18
<211> LENGTH: 17
<212> TYPE: DNA
<213> ORGANISM: Artificial Sequence
<220> FEATURE:
<223> OTHER INFORMATION: Amino acid sequence of primer for pUDR119 and
      pUDR164 construction

<400> SEQUENCE: 18
cgaccgagtt gctcttg                                                   17

<210> SEQ ID NO 19
<211> LENGTH: 20
<212> TYPE: DNA
<213> ORGANISM: Artificial Sequence
<220> FEATURE:
<223> OTHER INFORMATION: Amino acid sequence of primer for pUDR119 and
      pUDR164 construction

<400> SEQUENCE: 19
tattgacgcc gggcaagagc                                                20

```
<210> SEQ ID NO 20
<211> LENGTH: 120
<212> TYPE: DNA
<213> ORGANISM: Artificial Sequence
<220> FEATURE:
<223> OTHER INFORMATION: Amino acid sequence of primer for pUDR119
      construction

<400> SEQUENCE: 20
gttgataacg gactagcctt attttaactt gctatttcta gctctaaaac gaagaattcc      60
agtggtcaat gatcatttat ctttcactgc ggagaagttt cgaacgccga acatgcgca     120

<210> SEQ ID NO 21
<211> LENGTH: 120
<212> TYPE: DNA
<213> ORGANISM: Artificial Sequence
<220> FEATURE:
<223> OTHER INFORMATION: Amino acid sequence of primer for pUDR164
      construction

<400> SEQUENCE: 21
gttgataacg gactagcctt attttaactt gctatttcta gctctaaaac ctactctctt      60
cctagtcgcc gatcatttat ctttcactgc ggagaagttt cgaacgccga acatgcgca     120

<210> SEQ ID NO 22
<211> LENGTH: 40
<212> TYPE: DNA
<213> ORGANISM: Artificial Sequence
<220> FEATURE:
<223> OTHER INFORMATION: Addition of 20 bp primer-binding sequence to
      cbbM

<400> SEQUENCE: 22
gcgataccct gcgatcttca cagctatgac catgattacg                            40

<210> SEQ ID NO 23
<211> LENGTH: 38
<212> TYPE: DNA
<213> ORGANISM: Artificial Sequence
<220> FEATURE:
<223> OTHER INFORMATION: Addition of 20 bp primer-binding sequence to
      cbbM

<400> SEQUENCE: 23
cgcgcagatt agcgaagcct cactataggg cgaattgg                              38

<210> SEQ ID NO 24
<211> LENGTH: 81
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 24
acgcatctac gactgtgggt cccgtggaga aatgtatgaa accctgtatg gagagtgatt      60
gctggagctc agtttatcat t                                                81

<210> SEQ ID NO 25
<211> LENGTH: 80
<212> TYPE: DNA
<213> ORGANISM: Artificial Sequence
<220> FEATURE:
<223> OTHER INFORMATION: Amino acid sequence of primer for cbbM cassette
      construction
```

<400> SEQUENCE: 25
cgacgagatg ctcagactat gtgttctacc tgcttggaca tcttcgcgta tatgacggcc    60
cggccgcaaa ttaaagcctt                                                80

<210> SEQ ID NO 26
<211> LENGTH: 88
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 26
gcatagaaca ttatccgcgg aaacgggtat taggggtgag ggtgaataag gaaagtcagg    60
gaaatcgggc cgcgcagatt agcgaagc                                       88

<210> SEQ ID NO 27
<211> LENGTH: 79
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 27
aagggccatg accacctgat gcaccaatta ggtaggtctg gctatgtcta tacctctggc    60
gcgataccct gcgatcttc                                                 79

<210> SEQ ID NO 28
<211> LENGTH: 79
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 28
gtgcctattg atgatctggc ggaatgtctg ccgtgccata gccatgcctt cacatatagt    60
gcgataccct gcgatcttc                                                 79

<210> SEQ ID NO 29
<211> LENGTH: 78
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 29
gccagaggta tagacatagc cagacctacc taattggtgc atcaggtggt catggccctt    60
cgcgcagatt agcgaagc                                                  78

<210> SEQ ID NO 30
<211> LENGTH: 79
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 30
gttgaacatt cttaggctgg tcgaatcatt tagacacggg catcgtcctc tcgaaaggtg    60
gcgataccct gcgatcttc                                                79

<210> SEQ ID NO 31
<211> LENGTH: 78
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 31
actatatgtg aaggcatggc tatggcacgg cagacattcc gccagatcat caataggcac    60
cgcgcagatt agcgaagc                                                 78

<210> SEQ ID NO 32
<211> LENGTH: 79
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 32
ctagcgtgtc ctcgcatagt tcttagattg tcgctacggc atatacgatc cgtgagacgt    60
gcgataccct gcgatcttc                                                79

<210> SEQ ID NO 33
<211> LENGTH: 78
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 33
cacctttcga gaggacgatg cccgtgtcta aatgattcga ccagcctaag aatgttcaac    60
cgcgcagatt agcgaagc                                                 78

<210> SEQ ID NO 34
<211> LENGTH: 79
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 34
aatcactctc catacagggt ttcatacatt tctccacggg acccacagtc gtagatgcgt    60
gcgataccct gcgatcttc                                                79

<210> SEQ ID NO 35
<211> LENGTH: 78
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 35
acgtctcacg gatcgtatat gccgtagcga caatctaaga actatgcgag gacacgctag    60
cgcgcagatt agcgaagc                                                  78

<210> SEQ ID NO 36
<211> LENGTH: 79
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 36
acgcatctac gactgtgggt cccgtggaga aatgtatgaa accctgtatg gagagtgatt    60
gcgataccct gcgatcttc                                                 79

<210> SEQ ID NO 37
<211> LENGTH: 78
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 37
acgagagatg aaggctcacc gatggactta gtatgatgcc atgctggaag ctccggtcat    60
cgcgcagatt agcgaagc                                                  78

<210> SEQ ID NO 38
<211> LENGTH: 79
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 38
atgaccggag cttccagcat ggcatcatac taagtccatc ggtgagcctt catctctcgt    60
gcgataccct gcgatcttc                                                 79

<210> SEQ ID NO 39
<211> LENGTH: 78
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 39
ttctaggctt tgatgcaagg tccacatatc ttcgttagga ctcaatcgtg gctgctgatc    60
cgcgcagatt agcgaagc                                                  78

<210> SEQ ID NO 40
<211> LENGTH: 79
<212> TYPE: DNA
<213> ORGANISM: Artificial Sequence
<220> FEATURE:
<223> OTHER INFORMATION: Amino acid sequence of primer for cbbM cassette
      construction -continued

<400> SEQUENCE: 40
gatcagcagc cacgattgag tcctaacgaa gatatgtgga ccttgcatca aagcctagaa    60 gcgatacccct gcgatcttc    79

<210> SEQ ID NO 41
<211> LENGTH: 78
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 41
atactccctg cacagatgag tcaagctatt gaacaccgag aacgcgctga acgatcattc    60
cgcgcagatt agcgaagc    78

<210> SEQ ID NO 42
<211> LENGTH: 79
<212> TYPE: DNA
<213> ORGANISM: Artificial Sequence
<220> FEATURE:
<223> OTHER INFORMATION: Amino acid sequence of primer for cbbM cassette
      construction

<400> SEQUENCE: 42
gaatgatcgt tcagcgcgtt ctcggtgttc aatagcttga ctcatctgtg cagggagtat    60 gcgatacccct gcgatcttc    79

<210> SEQ ID NO 43
<211> LENGTH: 83
<212> TYPE: DNA
<213> ORGANISM: Artificial Sequence
<220> FEATURE:
<223> OTHER INFORMATION: Amino acid sequence of primer for groEL
      cassette construction

<400> SEQUENCE: 43
ggccgtcata tacgcgaaga tgtccaagca ggtagaacac atagtctgag catctcgtcg    60
cgaccatagc ttcaaaatgt ttc    83

<210> SEQ ID NO 44
<211> LENGTH: 83
<212> TYPE: DNA
<213> ORGANISM: Artificial Sequence
<220> FEATURE:
<223> OTHER INFORMATION: Amino acid sequence of primer for groEL
      cassette construction

<400> SEQUENCE: 44
gtcacgggtt ctcagcaatt cgagctatta ccgatgatgg ctgaggcgtt agagtaatct    60
gctcgacatt ttatgatgga atg    83

<210> SEQ ID NO 45
<211> LENGTH: 82
<212> TYPE: DNA
<213> ORGANISM: Artificial Sequence
<220> FEATURE:
<223> OTHER INFORMATION: Amino acid sequence of primer for groES
      cassette construction

<400> SEQUENCE: 45
agattactct aacgcctcag ccatcatcgg taatagctcg aattgctgag aacccgtgac    60
gggatctacg tatggtcatt tc                                            82

<210> SEQ ID NO 46
<211> LENGTH: 81
<212> TYPE: DNA
<213> ORGANISM: Artificial Sequence
<220> FEATURE:
<223> OTHER INFORMATION: Amino acid sequence of primer for groES
      cassette construction

<400> SEQUENCE: 46
tatatttgat gtaaatatct aggaaataca cttgtgtata cttctcgctt ttcttttatt    60
cgccctttta aacagttgat g                                             81

<210> SEQ ID NO 47
<211> LENGTH: 80
<212> TYPE: DNA
<213> ORGANISM: Artificial Sequence
<220> FEATURE:
<223> OTHER INFORMATION: Amino acid sequence of primer for DAN1p prk
      cassette construction

<400> SEQUENCE: 47
tcacagaggg atcccgttac ccatctatgc tgaagattta tcatactatt cctccgctcg    60
agaatgcaag ggcaaacagg                                               80

<210> SEQ ID NO 48
<211> LENGTH: 25
<212> TYPE: DNA
<213> ORGANISM: Artificial Sequence
<220> FEATURE:
<223> OTHER INFORMATION: Amino acid sequence of primer for DAN1p prk
      cassette construction

<400> SEQUENCE: 48
tacttggggt atatatttag tatgc                                         25

<210> SEQ ID NO 49
<211> LENGTH: 24
<212> TYPE: DNA
<213> ORGANISM: Artificial Sequence
<220> FEATURE:
<223> OTHER INFORMATION: Amino acid sequence of primer for prk cassette
      construction

<400> SEQUENCE: 49
attgaattga attgaaatcg atag                                          24

<210> SEQ ID NO 50
<211> LENGTH: 81
<212> TYPE: DNA
<213> ORGANISM: Artificial Sequence
<220> FEATURE:
<223> OTHER INFORMATION: Amino acid sequence of primer for prk cassette
      construction

<400> SEQUENCE: 50
aatcactctc catacagggt ttcatacatt tctccacggg acccacagtc gtagatgcgt    60
gcttcaagct tacacaacac g                                             81

```
<210> SEQ ID NO 51
<211> LENGTH: 81
<212> TYPE: DNA
<213> ORGANISM: Artificial Sequence
<220> FEATURE:
<223> OTHER INFORMATION: Amino acid sequence of primer for prk cassette
      construction

<400> SEQUENCE: 51
gtcataactc aatttgccta tttcttacgg cttctcataa aacgtcccac actattcagg      60
gcttcaagct tacacaacac g                                               81

<210> SEQ ID NO 52
<211> LENGTH: 50
<212> TYPE: DNA
<213> ORGANISM: Artificial Sequence
<220> FEATURE:
<223> OTHER INFORMATION: Amino acid sequence of primer for prk
      amplification

<400> SEQUENCE: 52
attgatctat cgatttcaat tcaattcaat ctaggcttta gcagctgttg                 50

<210> SEQ ID NO 53
<211> LENGTH: 81
<212> TYPE: DNA
<213> ORGANISM: Artificial Sequence
<220> FEATURE:
<223> OTHER INFORMATION: Amino acid sequence of primer for prk
      amplification

<400> SEQUENCE: 53
ttgcagataa aagtgtagca gataaaagtg tagcatacta aatatatacc ccaagtaatg      60
tcacaacaac aaacaattgt g                                               81

<210> SEQ ID NO 54
<211> LENGTH: 19
<212> TYPE: DNA
<213> ORGANISM: Artificial Sequence
<220> FEATURE:
<223> OTHER INFORMATION: Amino acid sequence of primer for 5'-INT1
      amplification

<400> SEQUENCE: 54
cggcattatt gtgtatggc                                                  19

<210> SEQ ID NO 55
<211> LENGTH: 24
<212> TYPE: DNA
<213> ORGANISM: Artificial Sequence
<220> FEATURE:
<223> OTHER INFORMATION: Amino acid sequence of primer for 3'-INT1
      amplification

<400> SEQUENCE: 55
cacaagctta ttcttccaaa aatc                                            24

<210> SEQ ID NO 56
<211> LENGTH: 73
<212> TYPE: DNA
<213> ORGANISM: Artificial Sequence
<220> FEATURE:
<223> OTHER INFORMATION: Amino acid sequence of primer for gRNA-INT1
      amplification
```

<400> SEQUENCE: 56
cttatcgata ccgtcgacct cgagggggg cccggtaccc agcttttgtt ccgcggtctt    60
tgaaaagata atg    73

<210> SEQ ID NO 57
<211> LENGTH: 69
<212> TYPE: DNA
<213> ORGANISM: Artificial Sequence
<220> FEATURE:
<223> OTHER INFORMATION: Amino acid sequence of primer for gRNA-INT1
      amplification

<400> SEQUENCE: 57
aaaatacaac aaataaaaaa cactcaatga cctgaccatt tgatggagtt ccgcggagac    60
ataaaaaac    69

<210> SEQ ID NO 58
<211> LENGTH: 20
<212> TYPE: DNA
<213> ORGANISM: Artificial Sequence
<220> FEATURE:
<223> OTHER INFORMATION: Amino acid sequence of primer for BB-1119
      amplification

<400> SEQUENCE: 58
aactccatca aatggtcagg    20

<210> SEQ ID NO 59
<211> LENGTH: 20
<212> TYPE: DNA
<213> ORGANISM: Artificial Sequence
<220> FEATURE:
<223> OTHER INFORMATION: Amino acid sequence of primer for BB-1119
      amplification

<400> SEQUENCE: 59
aacaaaagct gggtaccggg    20

<210> SEQ ID NO 60
<211> LENGTH: 70
<212> TYPE: DNA
<213> ORGANISM: Artificial Sequence
<220> FEATURE:
<223> OTHER INFORMATION: Amino acid sequence of primer for DAK1
      amplification

<400> SEQUENCE: 60
aaagccaaag ttcgcgttcc gaccttgcct cccaaatccg agttgcgatt gtgcgacacc    60
taactacata    70

<210> SEQ ID NO 61
<211> LENGTH: 70
<212> TYPE: DNA
<213> ORGANISM: Artificial Sequence
<220> FEATURE:
<223> OTHER INFORMATION: Amino acid sequence of primer for DAK1
      amplification

<400> SEQUENCE: 61
actcgaaagc agggaatcga actggagttg gactttcttc gggatcgggt gaggggagga    60
aatgagaaat    70

<210> SEQ ID NO 62
<211> LENGTH: 70
<212> TYPE: DNA
<213> ORGANISM: Artificial Sequence
<220> FEATURE:
<223> OTHER INFORMATION: Amino acid sequence of primer for gldA amplication

<400> SEQUENCE: 62

```
acccgatccc gaagaaagtc caactccagt tcgattccct gctttcgagt gtgcccgcgg    60
aaccgccaga                                                          70
```

<210> SEQ ID NO 63
<211> LENGTH: 70
<212> TYPE: DNA
<213> ORGANISM: Artificial Sequence
<220> FEATURE:
<223> OTHER INFORMATION: Amino acid sequence of primer for gldA amplication

<400> SEQUENCE: 63

```
tcgcttgcga aattcggaac tggcaagaat ctgggagaca aacggatact gaggacgatg    60
agagtgtaaa                                                          70
```

<210> SEQ ID NO 64
<211> LENGTH: 70
<212> TYPE: DNA
<213> ORGANISM: Artificial Sequence
<220> FEATURE:
<223> OTHER INFORMATION: Amino acid sequence of primer for T3 amplification

<400> SEQUENCE: 64

```
agtatccgtt tgtctcccag attcttgcca gttccgaatt tcgcaagcga ggagatatac    60
aatagaacag                                                          70
```

<210> SEQ ID NO 65
<211> LENGTH: 71
<212> TYPE: DNA
<213> ORGANISM: Artificial Sequence
<220> FEATURE:
<223> OTHER INFORMATION: Amino acid sequence of primer for T5 amplification

<400> SEQUENCE: 65

```
agtatccgtt tgtctcccag attcttgcca gttccgaatt tcgcaagcga gtgccaaaca    60
ttaatttgtt c                                                        71
```

<210> SEQ ID NO 66
<211> LENGTH: 71
<212> TYPE: DNA
<213> ORGANISM: Artificial Sequence
<220> FEATURE:
<223> OTHER INFORMATION: Amino acid sequence of primer for T3 amplification

<400> SEQUENCE: 66

```
gaaagaaatt gcgagcggat acggtggagg aaagttctgc cttgtattgg acgctgacat    60 ggtttctttag                                                         71
```

<210> SEQ ID NO 67
<211> LENGTH: 72
<212> TYPE: DNA
<213> ORGANISM: Artificial Sequence -continued

```
<220> FEATURE:
<223> OTHER INFORMATION: Amino acid sequence of primer for 5'-INT1
      amplification

<400> SEQUENCE: 67
aatcgcaact cggatttggg aggcaaggtc ggaacgcgaa ctttggcttt catgttatgc    60
tcctcaatca cg                                                       72

<210> SEQ ID NO 68
<211> LENGTH: 74
<212> TYPE: DNA
<213> ORGANISM: Artificial Sequence
<220> FEATURE:
<223> OTHER INFORMATION: Amino acid sequence of primer for 3'-INT1
      amplification

<400> SEQUENCE: 68
ccaatacaag gcagaacttt cctccaccgt atccgctcgc aatttcttc gaatgacctg    60 ttcccgacac tatg                                                     74
```

GLYCEROL FREE ETHANOL PRODUCTION

CROSS-REFERENCE TO RELATED APPLICATIONS

This application is a Continuation of U.S. patent application Ser. No. 17/204,018, filed 17 Mar. 2021, which is a Continuation of U.S. patent application Ser. No. 16/470,387, filed 17 Jun. 2019, which is a National Stage entry of International Application No. PCT/EP2017/083249, filed 18 Dec. 2017, which claims priority to European Patent Application Nos. 17193108.2, filed 26 Sep. 2017, and 16206564.3 filed 23 Dec. 2016. The content of each of these applications is herein incorporated by reference in their entirety.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_2919208-507002_ST25.txt" created on 11 Jun. 2021, and 66,988 bytes in size) is submitted concurrently with the instant application, and the entire contents of the Sequence Listing are incorporated herein by reference.

FIELD

The invention relates to a recombinant cell suitable for ethanol production, the use of this cell for the preparation of ethanol and/or succinic acid, and a process for preparing fermentation product using said recombinant cell.

BACKGROUND

Microbial fermentation processes are applied for industrial production of a broad and rapidly expanding range of chemical compounds from renewable carbohydrate feedstocks. Especially in anaerobic fermentation processes, redox balancing of the cofactor couple NADH/NAD$^+$ can cause important constraints on product yields. This challenge is exemplified by the formation of glycerol as major by-product in the industrial production of—for instance— fuel ethanol by *Saccharomyces cerevisiae*, a direct consequence of the need to reoxidize NADH formed in biosynthetic reactions. Ethanol production by *Saccharomyces cerevisiae* is currently, by volume, the single largest fermentation process in industrial biotechnology, but various other compounds, including other alcohols, carboxylic acids, isoprenoids, amino acids etc., are currently produced in industrial biotechnological processes. For conventional fermentative production of fuel ethanol, such as from corn starch and cane sugar, sugars predominantly occur as dimers or polymers of hexose sugars, which upon release in monosaccharides after pretreatment and enzymatic hydrolysis by different forms of glucohydrolases can be efficiently and rapidly fermented by *Saccharomyces cerevisiae*. Cellulosic or second generation bioethanol is produced from e.g. lignocellulosic fractions of plant biomass that is hydrolyzed intro free monomeric sugars, such as hexoses and pentoses, for fermentation into ethanol. Apart from the sugar release during pretreatment and hydrolysis of the biomass, some toxic by-products are formed depending on several pretreatment parameters, such as temperature, pressure and pretreatment time. Various approaches have been proposed to improve the fermentative properties of organisms used in industrial biotechnology by genetic modification. A major challenge relating to the stoichiometry of yeast-based production of ethanol, but also of other compounds, is that substantial amounts of NADH-dependent side-products (in particular glycerol) are generally formed as a by-product, especially under anaerobic and oxygen-limited conditions or under conditions where respiration is otherwise constrained or absent. It has been estimated that, in typical industrial ethanol processes, up to about 4 wt % of the sugar feedstock is converted into glycerol (Nissen et al. Yeast 16 (2000) 463-474). Under conditions that are ideal for anaerobic growth, the conversion into glycerol may even be higher, up to about 10%.

Glycerol production under anaerobic conditions is primarily linked to redox metabolism. During anaerobic growth of *S. cerevisiae*, sugar dissimilation occurs via alcoholic fermentation. In this process, the NADH formed in the glycolytic glyceraldehyde-3-phosphate dehydrogenase reaction is re-oxidized by converting acetaldehyde, formed by decarboxylation of pyruvate to ethanol via NAD$^+$ dependent alcohol dehydrogenase. The fixed stoichiometry of this redox-neutral dissimilatory pathway causes problems when a net reduction of NAD$^+$ to NADH occurs elsewhere in metabolism (e.g. biomass formation). Under anaerobic conditions, NADH re-oxidation in *S. cerevisiae* is strictly dependent on reduction of sugar to glycerol. Glycerol formation is initiated by reduction of the glycolytic intermediate dihydroxyacetone phosphate (DHAP) to glycerol 3-phosphate (glycerol-3P), a reaction catalyzed by NAD$^+$ dependent glycerol 3-phosphate dehydrogenase. Subsequently, the glycerol 3-phosphate formed in this reaction is hydrolysed by glycerol-3-phosphatase to yield glycerol and inorganic phosphate. Consequently, glycerol is a major by-product during anaerobic production of ethanol by *S. cerevisiae*, which is undesired as it reduces overall conversion of sugar to ethanol. Further, the presence of glycerol in effluents of ethanol production plants may impose costs for waste-water treatment.

WO2013/89878 describes a recombinant cell functionally heterologous nucleic acid sequences encoding for ribulose-1,5-phosphate carboxylase/oxygenase (EC 4.1.1.39; herein abbreviated as "RuBisCO"), and optionally molecular chaperones for RuBisCO, and phosphoribulokinase (EC 2.7.1.19; herein abbreviated as "PRK").

WO2015/107496 describes a recombinant cell functionally expressing heterologous nucleic acid sequences encoding for RuBisCO-units RbcL, RbcS and RcbX, molecular chaperones for Rubisco GroEL and GroES. In the examples PRK is expressed with a tetracyclin-inducible promoter TetO7.

SUMMARY

The invention relates to a recombinant cell suitable for ethanol production, the use of this cell for the preparation of ethanol and/or succinic acid, and a process for preparing fermentation product using said recombinant cell.

DETAILED DESCRIPTION

Figure 1:
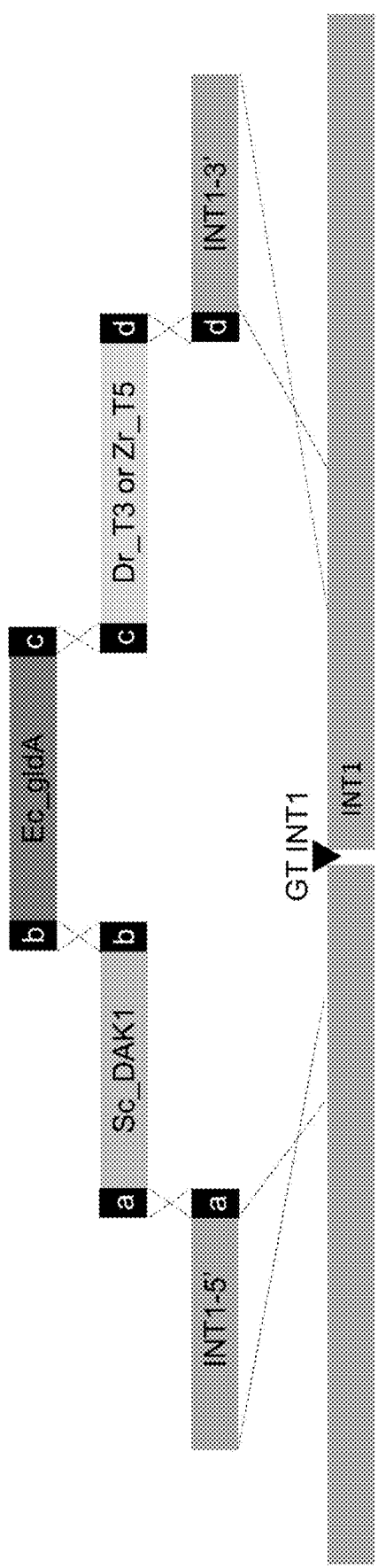
FIG. 1: Glycerol re-uptake pathway integrated at genomic locus INT1 with CRISPR-Cas9. The figure depicts the integration at the genomic site INT1 aided by the CRISPR-Cas9 methodology described in PCT/EP2016/050136. INT1-5': 500 bp 5'-integration flank for INT1 locus PCR-amplified from CEN.PK113-7D; Sc_DAK1: expression cassette Sc_DAK1 PCR-amplified from pDB1333; Ec_gldA: expression cassette E. coli gldA PCR-amplified from pDB1332; Dr_T3: *D. rerio* T3 glycerol transporter expression cassette; Zr_T5: *Z. rouxii* T5 glycerol transporter expression cassette PCR-amplified from pDB1336; INT1_3': 500 bp down stream integration flank for INT1-locus; (a)(b)(c)(d): 50 bp connector sequences flanking the different expression cassettes to enable correct assembly of the pathway at INT1; GT INT1: genomic target sequence for the Cas9 induced double strand break.

The term "a" or "an" as used herein is defined as "at least one" unless specified otherwise.

When referring to a noun (e.g. a compound, an additive, etc.) in the singular, the plural is meant to be included. Thus, when referring to a specific moiety, e.g. "gene", this means "at least one" of that gene, e.g. "at least one gene", unless specified otherwise. The term 'or' as used herein is to be understood as 'and/or'.

When referring to a compound of which several isomers exist (e.g. a D and an L enantiomer), the compound in principle includes all enantiomers, diastereomers and cis/trans isomers of that compound that may be used in the particular method of the invention; in particular when referring to such as compound, it includes the natural isomer(s).

The term 'fermentation', 'fermentative' and the like is used herein in a classical sense, i.e. to indicate that a process is or has been carried out under anaerobic conditions. Anaerobic conditions are herein defined as conditions without any oxygen or in which essentially no oxygen is consumed by the cell, in particular a yeast cell, and usually corresponds to an oxygen consumption of less than 5 mmol/l·h$^{-1}$, in particular to an oxygen consumption of less than 2.5 mmol/l·h$^{-1}$, or less than 1 mmol/l·h$^{-1}$. More preferably 0 mmol/L/h is consumed (i.e. oxygen consumption is not detectable. This usually corresponds to a dissolved oxygen concentration in the culture broth of less than 5% of air saturation, in particular to a dissolved oxygen concentration of less than 1% of air saturation, or less than 0.2% of air saturation.

The term "cell" refers to a eukaryotic or prokaryotic organism, preferably occurring as a single cell. The cell may be selected from the group of fungi, yeasts, euglenoids, archaea and bacteria.

The cell may in particular be selected from the group of genera consisting of yeast.

The term "yeast" or "yeast cell" refers to a phylogenetically diverse group of single-celled fungi, most of which are in the division of Ascomycota and Basidiomycota. The budding yeasts ("true yeasts") are classified in the order Saccharomycetales, with *Saccharomyces cerevisiae* as the most well-known species.

The term "recombinant (cell)" or "recombinant microorganism" as used herein, refers to a strain (cell) containing nucleic acid which is the result of one or more genetic modifications using recombinant DNA technique(s) and/or another mutagenic technique(s). In particular a recombinant cell may comprise nucleic acid not present in a corresponding wild-type cell, which nucleic acid has been introduced into that strain (cell) using recombinant DNA techniques (a transgenic cell), or which nucleic acid not present in said wild-type is the result of one or more mutations—for example using recombinant DNA techniques or another mutagenesis technique such as UV-irradiation—in a nucleic acid sequence present in said wild-type (such as a gene encoding a wild-type polypeptide) or wherein the nucleic acid sequence of a gene has been modified to target the polypeptide product (encoding it) towards another cellular compartment. Further, the term "recombinant (cell)" in particular relates to a strain (cell) from which DNA sequences have been removed using recombinant DNA techniques.

The term "transgenic (yeast) cell" as used herein, refers to a strain (cell) containing nucleic acid not naturally occurring in that strain (cell) and which has been introduced into that strain (cell) using recombinant DNA techniques, i.e. a recombinant cell).

The term "mutated" as used herein regarding proteins or polypeptides means that at least one amino acid in the wild-type or naturally occurring protein or polypeptide sequence has been replaced with a different amino acid, inserted or deleted from the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sambrook et al., Molecular Cloning-A Laboratory Manual, 2nd ed., Vol. 1-3 (1989). The term "mutated" as used herein regarding genes means that at least one nucleotide in the nucleic acid sequence of that gene or a regulatory sequence thereof, has been replaced with a different nucleotide, or has been deleted from the sequence via mutagenesis, resulting in the transcription of a protein sequence with a qualitatively of quantitatively altered function or the knock-out of that gene.

In the context of this invention an "altered gene" has the same meaning as a mutated gene.

The term "gene", as used herein, refers to a nucleic acid sequence containing a template for a nucleic acid polymerase, in eukaryotes, RNA polymerase II. Genes are transcribed into mRNAs that are then translated into protein.

The term "nucleic acid" as used herein, includes reference to a deoxyribonucleotide or ribonucleotide polymer, i.e. a polynucleotide, in either single or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulphation, gamma-carboxylation of glutamic acid residues, hydroxylation and ADP-ribosylation.

When an enzyme is mentioned with reference to an enzyme class (EC), the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at chem.qmul.ac.uk/iubmb/enzyme. Other suitable enzymes that have not (yet) been classified in a specified class but may be classified as such, are meant to be included.

If referred herein to a protein or a nucleic acid sequence, such as a gene, by reference to a accession number, this number in particular is used to refer to a protein or nucleic acid sequence (gene) having a sequence as can be found via ncbi.nlm.nih.gov, (as available on 14 Jun. 2016) unless specified otherwise.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, conservatively modified variants refers to those nucleic acids which encode identical or conservatively modified variants of the amino acid sequences due to the degeneracy of the genetic code. The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation.

The term "functional homologue" (or in short "homologue") of a polypeptide having a specific sequence (e.g. "SEQ ID NO: X"), as used herein, refers to a polypeptide comprising said specific sequence with the proviso that one or more amino acids are substituted, deleted, added, and/or inserted, and which polypeptide has (qualitatively) the same enzymatic functionality for substrate conversion. This functionality may be tested by use of an assay system comprising a recombinant cell comprising an expression vector for the expression of the homologue in yeast, said expression vector comprising a heterologous nucleic acid sequence operably linked to a promoter functional in the yeast and said heterologous nucleic acid sequence encoding the homologous polypeptide of which enzymatic activity for converting acetyl-Coenzyme A to acetaldehyde in the cell is to be tested, and assessing whether said conversion occurs in said cells. Candidate homologues may be identified by using in silico similarity analyses. A detailed example of such an analysis is described in Example 2 of WO2009/013159. The skilled person will be able to derive there from how suitable candidate homologues may be found and, optionally upon codon(pair) optimization, will be able to test the required functionality of such candidate homologues using a suitable assay system as described above. A suitable homologue represents a polypeptide having an amino acid sequence similar to a specific polypeptide of more than 50%, preferably of 60% or more, in particular of at least 70%, more in particular of at least 80%, at least 90%, at least 95%, at least 97%, at least 98% or at least 99% and having the required enzymatic functionality. With respect to nucleic acid sequences, the term functional homologue is meant to include nucleic acid sequences which differ from another nucleic acid sequence due to the degeneracy of the genetic code and encode the same polypeptide sequence.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably. A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labeled in the output of the program as "longest-identity".

A variant of a nucleotide or amino acid sequence disclosed herein may also be defined as a nucleotide or amino acid sequence having one or several substitutions, insertions and/or deletions as compared to the nucleotide or amino acid sequence specifically disclosed herein (e.g. in de the sequence listing).

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. In an embodiment, conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. In an embodiment, conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

Nucleotide sequences of the invention may also be defined by their capability to hybridise with parts of specific nucleotide sequences disclosed herein, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

"Expression" refers to the transcription of a gene into structural RNA (rRNA, tRNA) or messenger RNA (mRNA) with subsequent translation into a protein.

As used herein, "heterologous" in reference to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "heterologous expression" refers to the expression of heterologous nucleic acids in a host cell. The expression of heterologous proteins in eukaryotic host cell systems such as yeast are well known to those of skill in the art. A polynucleotide comprising a nucleic acid sequence of a gene encoding an enzyme with a specific activity can be expressed in such a eukaryotic system. In some embodiments, transformed/transfected cells may be employed as expression systems for the expression of the enzymes. Expression of heterologous proteins in yeast is well known. Sherman, F., et al., Methods in Yeast Genetics, Cold Spring Harbor Laboratory (1982) is a well-recognized work describing the various methods available to express proteins in yeast. Two widely utilized yeasts are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

As used herein "promoter" is a DNA sequence that directs the transcription of a (structural) gene. Typically, a promoter is located in the 5'-region of a gene, proximal to the transcriptional start site of a (structural) gene. Promoter sequences may be constitutive, inducible or repressible. In an embodiment there is no (external) inducer needed.

The term "vector" as used herein, includes reference to an autosomal expression vector and to an integration vector used for integration into the chromosome.

The term "expression vector" refers to a DNA molecule, linear or circular, that comprises a segment encoding a polypeptide of interest under the control of (i.e. operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular an expression vector comprises a nucleic acid sequence that comprises in the 5' to 3' direction and operably linked: (a) a yeast-recognized transcription and translation initiation region, (b) a coding sequence for a polypeptide of interest, and (c) a yeast-recognized transcription and translation termination region. "Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e. operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

By "host cell" is meant a cell which contains a vector and supports the replication and/or expression of the vector.

"Transformation" and "transforming", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome. By "disruption" is meant (or includes) all nucleic acid modifications such as nucleotide deletions or substitutions, gene knock-outs, (other) which affect the translation or transcription of the corresponding polypeptide and/or which affect the enzymatic (specific) activity, its substrate specificity, and/or stability. Such modifications may be targeted on the coding sequence or on the promotor of the gene.

The term "encoding" has the same meaning as "coding for". Thus, by way of example, "one or more heterologous genes encoding a glycerol dehydrogenase" has the same meaning as "one or more heterologous genes coding for a glycerol dehydrogenase". As far as genes encoding an enzyme are concerned, the phrase "one or more heterologous genes encoding a X", wherein X denotes an enzyme, has the same meaning as "one or more heterologous genes encoding an enzyme having X activity". Thus, by way of example, "one or more heterologous genes encoding a glycerol dehydrogenase" has the same meaning as "one or more heterologous genes encoding an enzyme having glycerol dehydrogenase activity".

In one aspect the invention provides a recombinant cell, preferably a yeast cell comprising:
a) one or more heterologous genes encoding a glycerol dehydrogenase,
b) one or more genes encoding a dihydroxyacetone kinase (E.C. 2.7.1.28 and/or E.C. 2.7.1.29);
c) one or more heterologous genes encoding a ribulose-1,5-biphosphate carboxylase oxygenase (RuBisCO; EC 4.1.1.39); and
d) one or more heterologous genes encoding a phosphoribulokinase (EC 2.7.1.19, PRK); and optionally
e) one or more heterologous genes encoding a glycerol transporter.

In an embodiment the glycerol dehydrogenase is preferably a NAD$^+$ linked glycerol dehydrogenase (EC 1.1.1.6). Such enzyme may be from bacterial origin or for instance from fungal origin. An example is gldA from *E. coli*.

Alternatively, the glycerol dehydrogenase may be a NADP$^+$ linked glycerol dehydrogenase (EC 1.1.1.72).

When the cell is used for ethanol production, which typically takes place under anaerobic conditions, a NAD$^+$ linked glycerol dehydrogenase is preferred.

In an embodiment the cell comprises one or more nucleic acid sequences encoding a heterologous glycerol dehydrogenase represented by amino acid sequence SEQ ID NO:13 or a functional homologue thereof a having sequence identity of at least 50%, preferably at least 60%, 70%, 75%, 80%, 85%, 90% or 95%.

In an embodiment the dihydroxy acetone kinase is encoded by an endogenous gene, e.g. a DAK1 gene, which endogenous gene is preferably placed under control of a constitutive promoter.

In an embodiment the cell comprises one or more nucleic acid sequences encoding a dihydroxy acetone kinase represented by amino acid sequence according to SEQ ID NO: 14 or by a functional homologue thereof having a sequence identity of at least 50%, preferably at least 60%, 70%, 75%, 80%, 85%, 90% or 95%, which gene is preferably placed under control of a constitutive promoter.

The dihydroxy acetone kinase may also have glyceraldehyde kinase activity.

WO2014/129898 discloses a yeast cell comprising one or more genes coding for ribulose-1,5-biphosphate carboxylase oxygenase (EC 4.1.1.39, RuBisCO); one or more genes coding for phosphoribulokinase (EC 2.7.1.19, PRK). The inventors have found that by introducing one or more genes encoding an NAD$^+$ linked glycerol dehydrogenase (EC 1.1.1.6 or EC 1.1.1.72), and one or more genes encoding a dihydroxyacetone kinase (E.C. 2.7.1.28 or E.C. 2.7.1.29); the ethanol yield can be increased. Glycerol may still be produced, but is, at least partially converted to ethanol.

One advantage of this invention is that glycerol production is reduced and/or the ethanol yield is increased. Without wanting to be bound by theory, the inventors think that this may be the result of re-oxidation of NADH by using $CO_2$ as electron acceptor (through RuBisCO), rather than produce glycerol.

In an embodiment, the cell comprises a genetic modification that increases the specific activity of dihydroxyacetone kinase in the cell. A dihydroxyacetone kinase is herein understood as an enzyme that catalyzes the chemical reaction ((EC 2.7.1.29):

Other names in common use include glycerone kinase, ATP:glycerone phosphotransferase and (phosphorylating) acetol kinase. It is understood that glycerone and dihydroxyacetone are the same molecule. Preferably said genetic modification causes overexpression of a dihydroxyacetone kinase, e.g. by overexpression of a nucleotide sequence encoding a dihydroxyacetone kinase. The nucleotide sequence encoding the dihydroxyacetone kinase may be endogenous to the cell or may be a dihydroxyacetone kinase that is heterologous to the cell. Nucleotide sequences that may be used for overexpression of dihydroxyacetone kinase in the cells of the invention are e.g. the dihydroxyacetone kinase genes from S. cerevisiae (DAK1) and (DAK2) as e.g. described by Molin et al. (2003, J. Biol. Chem. 278:1415-1423). In a preferred embodiment a codon-optimised (see above) nucleotide sequence encoding the dihydroxyacetone kinase is overexpressed, such as e.g. a codon optimised nucleotide sequence encoding the dihydroxyacetone kinase of SEQ ID NO: 14. A preferred nucleotide sequence for overexpression of a dihydroxyacetone kinase is a nucleotide sequence encoding a dihydroxyacetone kinase comprises an amino acid sequence with at least 45, 50, 60, 65, 70, 75, 80, 85, 90, 95, 98, 99% amino acid sequence identity with SEQ ID NO: 14 (S. cerevisiae (DAK1) or having one or several substitutions, insertions and/or deletions as compared to SEQ ID NO: 14.

Nucleotide sequences that may be used for overexpression of a heterologous dihydroxyacetone kinase in the cells of the invention are e.g. sequences encoding bacterial dihydroxyacetone kinases such as the dhaK gene from *Citrobacter freundii* e.g. described by Daniel et al. (1995, J. Bacteriol. 177:4392-4401).

For overexpression of the nucleotide sequence encoding the dihydroxyacetone kinase, the nucleotide sequence (to be overexpressed) is placed in an expression construct wherein it is operably linked to suitable expression regulatory regions/sequences to ensure overexpression of the dihydroxyacetone kinase enzyme upon transformation of the expression construct into the host cell of the invention (see above). Suitable promoters for (over)expression of the nucleotide sequence coding for the enzyme having dihydroxyacetone kinase activity include promoters that are preferably insensitive to catabolite (glucose) repression, that are active under anaerobic conditions and/or that preferably do not require xylose or arabinose for induction. Examples of such promoters are given above. A dihydroxyacetone kinase to be overexpressed is preferably overexpressed by at least a factor 1.1, 1.2, 1.5, 2, 5, 10 or 20 as compared to a strain which is genetically identical except for the genetic modification causing the overexpression. Preferably, the dihydroxyacetone kinase is overexpressed under anaerobic conditions by at least a factor 1.1, 1.2, 1.5, 2, 5, 10 or 20 as compared to a strain which is genetically identical except for the genetic modification causing the overexpression. It is to be understood that these levels of overexpression may apply to the steady state level of the enzyme's activity (specific activity in the cell), the steady state level of the enzyme's protein as well as to the steady state level of the transcript coding for the enzyme in the cell. Overexpression of the nucleotide sequence in the host cell produces a specific dihydroxyacetone kinase activity of at least 0.002, 0.005, 0.01, 0.02 or 0.05 U min-1 (mg protein)-1, determined in cell extracts of the transformed host cells at 30° C. as described e.g. in the Examples of WO2013/081456.

In an embodiment the cell comprises a heterologous gene encoding a dihydroxyacetone kinase. Suitable dihydroxyacetone kinases are from *Saccharomyces kudriavzevii, Zygosaccharomyces bailii, Kluyveromyces lactis, Candida glabrata, Yarrowia lipolytica, Klebsiella pneumoniae, Enterobacter aerogenes, Escherichia coli, Yarrowia lipolytica, Schizosaccharomyces pombe, Botryotinia fuckeliana,* and *Exophiala dermatitidis.*

The cell optionally comprises one or more heterologous genes encoding a glycerol transporter. In this embodiment any glycerol that is externally available in the medium (e.g. from the backset in corn mash) or secreted after internal cellular synthesis may be transported into the cell and converted to ethanol.

In an embodiment the cell comprises a deletion or disruption of one or more endogenous nucleotide sequences encoding a glycerol exporter (e.g FPS1).

In a further embodiment, the cell naturally lacks enzymatic activity needed for the NADH-dependent glycerol synthesis, for example yeast cells belonging to the species *Brettanomyces intermedius.*

In an embodiment the cell comprises a deletion or disruption of one or more endogenous nucleotide sequences encoding a glycerol 3-phosphate phosphohydrolase and/or encoding a glycerol-3-phosphate dehydrogenase. Such a deletion or disruption may result in decrease or removal of enzymatic activity. The deleted or disrupted glycerol-3-phosphate dehydrogenase preferably belongs to EC 1.1.5.3, such as GUT2, or to EC 1.1.1.8, such as PDP1 and or PDP2.

In embodiment the cell is free of genes encoding NADH-dependent glycerol-3-phosphate dehydrogenase.

In another embodiment the cell comprises a deletion or disruption of one or more endogenous nucleotide sequences encoding a glycerol kinase (EC 2.7.1.30). An example of such an enzyme is Gut1p.

The cell may be free of enzymatic activity needed for the NADH-dependent glycerol synthesis or has a reduced enzymatic activity with respect to the NADH-dependent biochemical pathway for glycerol synthesis from a carbohydrate compared to its corresponding wild-type cell.

A reduced enzymatic activity can be achieved by modifying one or more genes encoding a NAD-dependent glycerol 3-phosphate dehydrogenase activity (GPD) or one or more genes encoding a glycerol phosphate phosphatase activity (GPP), such that the enzyme is expressed considerably less than in the wild-type or such that the gene encodes a polypeptide with reduced activity. Such modifications can be carried out using commonly known biotechnological techniques, and may in particular include one or more knock-out mutations or site-directed mutagenesis of promoter regions or coding regions of the structural genes encoding GPD and/or GPP. Alternatively, strains that are defective in glycerol production may be obtained by random mutagenesis followed by selection of strains with reduced or absent activity of GPD and/or GPP. Examples of genes in *S. cerevisiae* encoding GPD-activity are GPD1, GPD2, and GPP-activity are GPP1 and GPP2.

GPD and/or GPP may be entirely deleted, or at least a part is deleted which encodes a part of the enzyme that is essential for its activity. In particular, good results have been achieved with a *S. cerevisiae* cell, wherein the open reading frames of the GPD1 gene and of the GPD2 gene have been inactivated. Inactivation of a structural gene (target gene) can be accomplished by a person skilled in the art by synthetically synthesizing or otherwise constructing a DNA fragment consisting of a selectable marker gene flanked by DNA sequences that are identical to sequences that flank the region of the host cell's genome that is to be deleted. In particular, good results have been obtained with the inactivation of the GPD1 and GPD2 genes in *Saccharomyces*

*cerevisiae* by integration of the marker genes kanMX and hphMX4. Subsequently this DNA fragment is transformed into a host cell. Transformed cells that express the dominant marker gene are checked for correct replacement of the region that was designed to be deleted, for example by a diagnostic polymerase chain reaction or Southern hybridization.

In an embodiment the cell comprises one or more nucleic acid sequences encoding a heterologous glycerol transporter represented by amino acid sequence SEQ ID NO:7 or a functional homologue thereof having a sequence identity of at least 50%, preferably at least 60%, 70%, 75%, 80%, 85%, 90% or 95%.

In an embodiment the cell comprises one or more nucleic acid sequences encoding a heterologous glycerol transporter represented by amino acid sequence SEQ ID NO:8 or a functional homologue thereof having a sequence identity of at least 50%, preferably at least 60%, 70%, 75%, 80%, 85%, 90% or 95%.

In an embodiment the cell a yeast cell. The cell may be selected from Saccharomycetaceae, in particular from the group of *Saccharomyces*, such as *Saccharomyces cerevisiae*; *Kluyveromyces*, such as *Kluyveromyces marxianus*; *Pichia*, such as *Pichia stipitis* or *Pichia angusta*; *Zygosaccharomyces*, such as *Zygosaccharomyces bailii*; and *Brettanomyces*, such as *Brettanomyces intermedius*, *Issatchenkia*, such as *Issatchenkia orientalis* and *Hansenula*.

In another embodiment the cell is a prokaryotic cell, such as selected from the list consisting of *Clostridium*, *Zymomonas*, *Thermobacter*, *Escherichia*, *Lactobacillus*, *Geobacillus* and *Bacillus*.

In an embodiment the cell comprises one or more genes, preferably a heterologous genes, coding for molecular chaperones, said chaperones preferably originating from a prokaryote, more preferably a bacterium, even more preferably *E. coli*.

Chaperones—when expressed—are preferably capable of functionally interacting with an enzyme in the microorganism, in particular with at least one of Rubisco and PRK. Chaperones are proteins that provide favourable conditions for the correct folding of other proteins, thus preventing aggregation. Newly made proteins usually must fold from a linear chain of amino acids into a three-dimensional form. Chaperon ins belong to a large class of molecules that assist protein folding, called molecular chaperones. The energy to fold proteins is supplied by adenosine triphosphate (ATP). A review article about chaperones that is useful herein is written by Yebenes (2001); "Chaperonins: two rings for folding"; Hugo Yebenes et al. Trends in Biochemical Sciences, August 2011, Vol. 36, No. 8.

In an embodiment, the one or more chaperone is from a bacterium, more preferably from *Escherichia*, in particular *E. coli* GroEL and GroES from *E. coli* may in particular encoded in a microorganism according to the invention. Other preferred chaperones are chaperones from *Saccharomyces*, in particular *Saccharomyces cerevisiae* Hsp10 and Hsp60. If the chaperones are naturally expressed in an organelle such as a mitochondrion (examples are Hsp60 and Hsp10 of *Saccharomyces cerevisiae*) relocation to the cytosol can be achieved e.g. by modifying the native signal sequence of the chaperonins.

In eukaryotes the proteins Hsp60 and Hsp10 are structurally and functionally nearly identical to GroEL and GroES, respectively. Thus, it is contemplated that Hsp60 and Hsp10 from any eukaryotic cell may serve as a chaperone for the Rubisco. See Zeilstra-Ryalls J, Fayet O, Georgopoulos C (1991). "The universally conserved GroE (Hsp60) chaperonins". Annu Rev Microbiol. 45: 301-25. doi:10.1146/annurev.mi.45.100191.001505. PMID 1683763 and Horwich A L, Fenton W A, Chapman E, Farr G W (2007). "Two Families of Chaperonin: Physiology and Mechanism". Annu Rev Cell Dev Biol. 23: 115-45. doi:10.1146/annurev.cellbio.23.090506.123555. PMID 17489689.

As an alternative to GroEL a functional homologue of GroEL may be present, in particular a functional homologue comprising an amino acid sequence having at least 70%, 75%, 80%, 85%, 90% or 95% sequence identity with SEQ ID NO: 10. Suitable natural chaperones polypeptides homologous to SEQ ID NO: 10 are given in Table 4 of WO2014/129898.

As an alternative to GroES a functional homologue of GroES may be present, in particular a functional homologue comprising an amino acid sequence having at least 70%, 75%, 80%, 85%, 90% or 95% sequence identity with SEQ ID NO: 9. Suitable natural chaperones polypeptides homologous to SEQ ID NO: 9 are given in Table 3 of WO2014/129898.

In an embodiment, a 10 kDa chaperone from Table 3 of WO2014/129898 is combined with a matching 60 kDa chaperone from Table 4 from WO2014/129898 of the same organism genus or species for expression in the host. For instance: >gi|189189366|ref|XP_001931022.1|:71-168 10 kDa chaperonin [*Pyrenophora tritici-repentis*] expressed together with matching >gi|189190432|ref|XP_001931555.1| heat shock protein 60, mitochondrial precursor [*Pyrenophora tritici-repentis* Pt-1C-BFP].

All other combinations from Table 3 and 4 of WO2014/129898 similarly made with same organism source are also available to the skilled person for expression.

The RuBisCO may in principle be selected from eukaryotic and prokaryotic RuBisCO's. The RuBisCO is preferably from a non-phototrophic organism. In particular, the RuBisCO may be from a chemolithoautotrophic microorganism. Good results have been achieved with a bacterial RuBisCO. Preferably, the bacterial RuBisCO originates from a *Thiobacillus*, in particular, *Thiobacillus denitrificans*, which is chemolithoautotrophic. The RuBisCO may be a single-subunit RuBisCO or a RuBisCO having more than one subunit. In particular, good results have been achieved with a single-subunit RuBisCO.

In particular, good results have been achieved with a form-II RuBbisCO, more in particular CbbM.

SEQ ID NO: 11 shows a sequence of a RuBisCO. It is encoded by the cbbM gene from *Thiobacillus denitrificans*. An alternative to this Rubisco is a functional homologue of this RuBisCO, in particular such functional homologue comprising an amino acid sequence having at least 80%, 85%, 90% or 95% sequence identity with SEQ ID NO: 11. Suitable natural RuBisCO polypeptides are given in Table 1 of WO2014/129898.

The RuBisCO is preferably functionally expressed in the cell, at least during use in an industrial process for preparing a compound of interest.

In an embodiment the functionally expressed RuBisCO has an activity, defined by the rate of ribulose-1,5-bisphosphate-dependent $^{14}$C-bicarbonate incorporation by cell extracts of at least 1 nmol·min$^{-1}$·(mg protein)$^{-1}$, in particular an activity of at least 2 nmol·min$^{-1}$·(mg protein)$^{-1}$, more in particular an activity of at least 4 nmol·min$^{-1}$·(mg protein)$^{-1}$. The upper limit for the activity is not critical. In practice, the activity may be about 200 nmol·min$^{-1}$·(mg protein)$^{-1}$ or less, in particular 25 nmol·min$^{-1}$·(mg protein)$^{-1}$, more in particular 15 nmol·min$^{-1}$·(mg protein)$^{-1}$ or less, e.g. about 10 nmol·min$^{-1}$·(mg protein)$^{-1}$ or less. The conditions for an assay for determining this Rubisco activity are as found in Example 4 of WO2014/129898.

In an embodiment the PRK is originating from a plant selected from Caryophyllales, in particular from Amaranthaceae, in particular from *Spinacia*.

In an embodiment the cell comprises one or more nucleic acid sequences encoding a PRK represented by amino acid sequence represented by SEQ ID NO: 12 or by a functional homologue thereof having sequence identity of at least 50%, preferably at least 60%, 70%, 75%, 80%, 85%, 90% or 95%.

A functionally expressed phosphoribulokinase (PRK, EC 2.7.1.19) is capable of catalysing the chemical reaction:

ATP+D-ribulose 5-phosphate ADP+D-ribulose 1,5-bisphosphate (I)

Thus, the two substrates of this enzyme are ATP and D-ribulose 5-phosphate, whereas its two products are ADP and D-ribulose 1,5-bisphosphate.

PRK belongs to the family of transferases, specifically those transferring phosphorus-containing groups (phosphotransferases) with an alcohol group as acceptor. The systematic name of this enzyme class is ATP:D-ribulose-5-phosphate 1-phosphotransferase. Other names in common use include phosphopentokinase, ribulose-5-phosphate kinase, phosphopentokinase, phosphoribulokinase (phosphorylating), 5-phosphoribulose kinase, ribulose phosphate kinase, PKK, PRuK, and PRK. This enzyme participates in carbon fixation.

The PRK can be from a prokaryote or a eukaryote. Good results have been achieved with a PRK originating from a eukaryote. Preferably the eukaryotic PRK originates from a plant selected from Caryophyllales, in particular from Amaranthaceae, more in particular from *Spinacia*.

As an alternative to PRK from *Spinacia* a functional homologue of PRK from *Spinacia* may be present, in particular a functional homologue comprising a sequence having at least 70%, 75%, 80%. 85%, 90% or 95% sequence identity with the PRK from *Spinacia*.

The one or more PRK genes may be under the control of a promoter (the "PRK promoter") that enables higher expression under anaerobic conditions than under aerobic conditions.

In an embodiment the PRK promoter is ROX1 repressed. ROX1 is herein haeme-dependent repressor of hypoxic gene(s); that mediates aerobic transcriptional repression of hypoxia induced genes such as COX5b and CYC7; the repressor function is regulated through decreased promoter occupancy in response to oxidative stress; and contains an HMG domain that is responsible for DNA bending activity; involved in the hyperosmotic stress resistance. ROX1 is regulated by oxygen.

According to Kwast et al. (in: Genomic Analysis of Anaerobically induced genes in *Saccharomyces cerevisiae*: Functional roles of ROX1 and other factors in mediating the anoxic response, 2002, Journal of bacteriology vol 184, no 1 p 250-265): "Although Rox1 functions in an O$_2$-independent manner, its expression is oxygen (haeme) dependent, activated by the haeme-dependent transcription factor Hap1 [Keng, T. 1992. *HAP1 and ROX1 form a regulatory pathway in the repression of HEM13 transcription in Saccharomyces cerevisiae. Mol. Cell. Biol.* 12: 2616-2623]. Thus, as oxygen levels fall to those that limit haeme biosynthesis [Labbe-Bois, R., and P. Labbe. 1990. *Tetrapyrrole and heme biosynthesis in the yeast Saccharomyces cerevisiae*, p. 235-285. In H. A. Dailey (ed.), Biosynthesis of heme and chlorophylls. McGraw-Hill, New York, N.Y], ROX1 is no longer transcribed [Zitomer, R. S., and C. V. Lowry. 1992. *Regulation of gene expression by oxygen in Saccharomyces cerevisiae. Microbiol. Rev.* 56:1-11], its protein levels fall [Zitomer, R. S., P. Carrico, and J. Decked. 1997. *Regulation of hypoxic gene expression in yeast. Kidney Int* 51:507-513], and the genes it regulates are de-repressed."

In an embodiment, the PRK promoter is ROX1-repressed. In an embodiment, the PRK promoter has one or more ROX1 binding motif.

In an embodiment, the PRK promoter comprises in its sequence one or more of the motif according to SEQ ID NO: 15.

In an embodiment, the PRK promoter is the native promoter of a gene selected from the list consisting of: FET4, ANB1, YHR048W, DAN1, AAC3, TIR2, DIP5, HEM13, YNR014W, YAR028W, FUN 57, COX5B, OYE2, SUR2, FRDS1, PIS1, LAC1, YGR035C, YAL028W, EUG1, HEM14, ISU2, ERG26, YMR252C and SML1, in particular FET4, ANB1, YHR048W, DAN1, AAC3, TIR2, DIP5 and HEM13.

In an embodiment, the PRK promoter comprises in its sequence one or more of the motif: TCGTTYAG and/or according to SEQ ID NO: 16.

In particular such PRK promoter is native promoter of a DAN, TIR or PAU gene. In an embodiment, the PRK promoter is the native promoter of a gene selected from the list consisting of: TIR2, DAN1, TIR4, TIR3, PAU7, PAU5, YLL064C, YGR294W, DAN3, YIL176C, YGL261C, YOL161C, PAU1, PAU6, DAN2, YDR542W, YIR041W, YKL224C, PAU3, YLL025W, YOR394W, YHL046C, YMR325W, YAL068C, YPL282C, PAU2, PAU4, in particular the PRK promoter is the native promoter of a gene selected from the list consisting of: TIR2, DAN1, TIR4, TIR3, PAU7, PAU5, YLL064C, YGR294W, DAN3, YIL176C, YGL261C, YOL161C, PAU1, PAU6, DAN2, YDR542W, YIR041W, YKL224C, PAU3, YLL025W.

In an embodiment, the promoter has a PRK expression ratio anaerobic/aerobic of 2 or more, 3 or more, 4 or more, 5 or more, 6 or more, 7 or more, 8 or more, 9 or more, 10 or more, 20 or more or 50 or more.

As used herein "promoter" is a DNA sequence that directs the transcription of a (structural) gene, herein in particular one or more phosphoribulokinase gene. The promoter enables higher expression during anaerobic conditions than under aerobic conditions.

In an embodiment, the PRK promoter may be a synthetic oligonucleotide. It may be a product of artificial oligonucleotide synthesis. Artificial oligonucleotide synthesis is a method in synthetic biology that is used to create artificial oligonucleotides, such as genes, in the laboratory. Commercial gene synthesis services are now available from numerous companies worldwide, some of which have built their business model around this task. Current gene synthesis approaches are most often based on a combination of organic chemistry and molecular biological techniques and entire genes may be synthesized "de novo", without the need for precursor template DNA.

In an embodiment, the promoter is located in the 5' region of a the PRK gene, In an embodiment it is located proximal to the transcriptional start site of PRK gene.

The invention further relates to a vector (as defined hereinafter) comprising PRK and a promoter that enables higher expression during anaerobic conditions than under aerobic conditions.

The PRK promoter may have a PRK expression ratio anaerobic/aerobic of 2 or more, 3 or more, 4 or more, 5 or more, 6 or more, 7 or more, 8 or more, 9 or more, 10 or more, 20 or more or 50 or more.

In an embodiment the PRK promoter is a synthetic oligonucleotide. The PRK promoter preferably enables expression only during anaerobic conditions.

A suitable PRK promotor is ANB1 and/or DAN1 as mentioned in EP16174382.8.

The cell may contain genes of a pentose metabolic pathway non-native to the cell and/or that allow the recombinant cell to convert pentose(s). In one embodiment, the cell may comprise one or two or more copies of one or more xylose isomerases and/or one or two or more copies of one or more xylose reductase and xylitol dehydrogenase genes, allowing the recombinant cell to convert xylose. In an embodiment thereof, these genes may be integrated into the recombinant cell genome. In another embodiment, the recombinant cell comprises the genes araA, araB and araD. It is then able to ferment arabinose. In one embodiment of the invention the recombinant cell comprises xylA-gene, XYL1 gene and XYL2 gene and/or XKS1-gene, to allow the recombinant cell to ferment xylose; deletion of the aldose reductase (GRE3) gene; overexpression of one or more PPP-genes, e.g. TAL1, TAL2, TKL1, TKL2, RPE1 and RKI1 to allow the increase of the flux through the pentose phosphate path-way in the cell, and/or overexpression of GAL2 and/or deletion of GAL80. Thus though inclusion of the above genes, suitable pentose or other metabolic pathway(s) may be introduced in the recombinant cell that were non-native in the (wild type) recombinant cell.

In an embodiment, the following genes may be introduced in the recombinant cell by introduction into a host cell:
1) a set consisting of PPP-genes TAL1, TKL1, RPE1 and RKI1, optionally under control of strong constitutive promoter;
2) a set consisting of a xylA-gene under under control of strong constitutive promoter;
3) a set comprising a XKS1-gene under control of strong constitutive promoter,
4) a set consisting of the bacterial genes araA, araB and araD under control of a strong constitutive promoter,
5) deletion of an aldose reductase gene The above cells may be constructed using known recombinant expression techniques. The cofactor modification may be effected before, simultaneous or after any of the modifications 1-5 above.

The cell according to the invention may be subjected to evolutionary engineering to improve its properties. Evolutionary engineering processes are known processes. Evolutionary engineering is a process wherein industrially relevant phenotypes of a microorganism, herein the recombinant cell, can be coupled to the specific growth rate and/or the affinity for a nutrient, by a process of rationally set-up natural selection. Evolutionary Engineering is for instance described in detail in Kuijper, M, et al, FEMS, Eukaryotic cell Research 5(2005) 925-934, WO2008041840 and WO2009112472. After the evolutionary engineering the resulting pentose fermenting recombinant cell is isolated. The isolation may be executed in any known manner, e.g. by separation of cells from a recombinant cell broth used in the evolutionary engineering, for instance by taking a cell sample or by filtration or centrifugation.

In an embodiment, the cell is marker-free. As used herein, the term "marker" refers to a gene encoding a trait or a phenotype which permits the selection of, or the screening for, a host cell containing the marker. Marker-free means that markers are essentially absent in the recombinant cell. Being marker-free is particularly advantageous when antibiotic markers have been used in construction of the recombinant cell and are removed thereafter. Removal of markers may be done using any suitable prior art technique, e.g. intramolecular recombination.

In one embodiment, the cell is constructed on the basis of an inhibitor tolerant host cell, wherein the construction is conducted as described hereinafter. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant S. cerevisiae strain ATCC 26602 was selected.

To increase the likelihood that enzyme activity is expressed at sufficient levels and in active form in the cell, the nucleotide sequence encoding these enzymes, as well as the RuBisCO enzyme and other enzymes of the disclosure are preferably adapted to optimise their codon usage to that of the cell in question.

The adaptiveness of a nucleotide sequence encoding an enzyme to the codon usage of a cell may be expressed as codon adaptation index (CAI). The codon adaptation index is herein defined as a measurement of the relative adaptiveness of the codon usage of a gene towards the codon usage of highly expressed genes in a particular cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51). An adapted nucleotide sequence preferably has a CAI of at least 0.2, 0.3, 0.4, 0.5, 0.6, 0.7, 0.8 or 0.9. Most preferred are the sequences which have been codon optimised for expression in the host cell in question such as e.g. S. cerevisiae cells.

In an embodiment the invention provides a recombinant S. cerevisae cell comprising:
a) one or more heterologous genes encoding a glycerol dehydrogenase,
b) one or more genes encoding a dihydroxyacetone kinase (E.C. 2.7.1.28 and/or E.C. 2.7.1.29);
c) one or more heterologous genes encoding a ribulose-1,5-biphosphate carboxylase oxygenase (RuBisCO; EC 4.1.1.39);
d) one or more heterologous genes encoding a phosphoribulokinase (EC 2.7.1.19, PRK);
e) one or more heterologous genes encoding a molecular chaperone; and
f) one or more heterologous genes encoding a glycerol transporter;
wherein said cell comprises:
g) a deletion or disruption of one or more endogenous nucleotide sequences encoding a glycerol-3-phosphate dehydrogenase.

In another embodiment the invention includes a recombinant S. cerevisae cell comprising:
a) one or more heterologous genes encoding a glycerol dehydrogenase represented by amino acid sequence SEQ ID NO: 13 or a functional homologue thereof a having sequence identity of at least 50%;
b) one or more genes encoding a dihydroxyacetone kinase represented by amino acid sequence according to SEQ ID NO: 14 or by a functional homologue thereof having a sequence identity of at least 50%, which gene is placed under control of a constitutive promoter;

c) one or more heterologous genes encoding a RubisCo represented by amino acid sequence according to SEQ ID NO: 11 or a functional homologue thereof having a sequence identity of at least 80%; and
d) one or more heterologous genes encoding groES represented by amino acid sequence according to SEQ ID NO: 9 or a functional homologue thereof having a sequence identity of at least 70% and/or groEL represented by amino acid sequence according to SEQ ID NO: 10 or a functional homologue thereof having a sequence identity of at least 70%;
e) one or more heterologous genes encoding a PRK as represented SEQ ID NO: 12 or a functional homologue thereof having a sequence identity of at least 50%; and optionally
f) one or more genes heterologous encoding a glycerol transporter represented by amino acid sequence according to SEQ ID NO: 7 or by a functional homologue thereof having a sequence identity of at least 50% and/or a glycerol transported represented by amino acid sequence according to SEQ ID NO: 8 or by a functional homologue thereof having a sequence identity of at least 50%;

wherein said cell comprises:
g) a deletion or disruption of one or more endogenous nucleotide sequences encoding a glycerol-3-phosphate dehydrogenase.

The invention further provides the use of a cell according to the invention for preparation of ethanol.

The invention also provides the use of a cell according to the invention for preparation of succinic acid.

The invention further provides a process for preparing fermentation product, comprising preparing a fermentation product from a fermentable carbohydrate, in particular selected from the group of glucose, fructose, sucrose, maltose, xylose, arabinose, galactose and mannose which preparation is carried out under anaerobic conditions using a cell according to the invention.

In an embodiment the fermentable carbohydrate is obtained from starch, lignocellulose, and/or pectin.

The starch, lignocellulose, and/or pectin may be contacted with an enzyme composition, wherein one or more sugar is produced, and wherein the produced sugar is fermented to give a fermentation product, wherein the fermentation is conducted with a cell of the invention.

The fermentation product may be one or more of ethanol, butanol, succinic acid, lactic acid, a plastic, an organic acid, a solvent, an animal feed supplement, a pharmaceutical, a vitamin, an amino acid, an enzyme or a chemical feedstock.

The process is particularly useful when glycerol is fed externally to the process, such as crude glycerol from transesterification-based biodiesel production or recirculation of backset, which is then taken up and converted to ethanol by the claimed cell.

EXAMPLES

Material and Methods

General Molecular Biology Techniques

Unless indicated otherwise, the methods used are standard biochemical techniques. Examples of suitable general methodology textbooks include Sambrook et al., Molecular Cloning, a Laboratory Manual (1989) and Ausubel et al., Current Protocols in Molecular Biology (1995), John Wiley & Sons, Inc.

Plasmids, Oligonucleotide Primers and Strains

Plasmids used in the examples are listed in Table 1. Primers used in the examples are listed in Table 2. Strains used for further strain engineering are listed in Table 3.

Media

Media used in the experiments were YEPh-medium (10 g/l yeast extract, 20 g/l phytone) and solid YNB-medium (6.7 g/l yeast nitrogen base, 15 g/l agar), supplemented with sugars as indicated in the examples. For solid YEPh medium, 15 g/l agar was added to the liquid medium prior to sterilization.

In the microaerobic or anaerobic cultivation experiments, Mineral Medium was used. The composition of Mineral Medium has been described by Verduyn et al., (Yeast, 1992, volume 8, pp. 501-517). Ammoniumsulphate was replaced by, 2.3 g/l urea as a nitrogen source. Initial pH of the medium was 4.6. In addition, for micro-/anaerobic experiments, ergosterol (0.01 g/L), Tween80 (0.42 g/L) and sugars (as indicated in examples) were added.

Micro-/Anaerobic Cultivations

Strains were semi-aerobically propagated in a 100 mL Erlenmeyer shake flask without baffle and with foam plug with 10 mL YEPh medium supplemented with 20 g/L glucose. Shake flasks were incubated 24 h at 30° C. at a shaking speed of 280 rpm. Pre-cultured cells were pelleted, washed and re-suspended with 1 culture volume sterilized water. A volume of re-suspended culture containing sufficient cell mass to inoculate the main fermentation medium to 75 mg of yeast (dry weight) per liter (see further below), was pelleted and and re-suspended into main fermentation medium.

To determine inoculum, a calibration curve was made of the IMX774 strain of biomass vs. OD600. This calibration curve was used to determine the volume of re-suspended cell culture to be processed to inoculum for 75 mg/L of yeast (dry weight).

Fermentation experiments were performed in an Alcoholic Fermentation Monitor (AFM, Applikon, Delft, The Netherlands), using 500 ml bottles filled to 400 ml with Mineral Medium containing ca. 50 g/L glucose. Fermentation temperature was maintained at 32° C. and stirred at 250 rpm, the pH was not controlled during fermentation. In addition to the online recording of $CO_2$ production by the AFM (correlating with ethanol (EtOH)), samples were taken with at intervals of 4 hours during the fermentation to monitor yeast biomass, substrate utilization- and product formation. Total fermentation time was 32 hours.

Samples for HPLC analysis were separated from yeast biomass by passing through a 0.2 μm pore size filter.

HPLC Analysis

HPLC analysis was conducted as described in "*Determination of sugars, byproducts and degradation products in liquid fraction in process sample*"; Laboratory Analytical Procedure (LAP, Issue date: Dec. 8, 2006; by A. Sluiter, B. Hames, R. Ruiz, C. Scarlata, J. Sluiter, and D. Templeton; Technical Report (NREL/TP-51042623); January 2008; National Renewable Energy Laboratory.

Strain Construction IMX774 and IME324

The strains generated and cultivated in the examples were transformants of strain IMX581 or IMX774. IMX581 is a CEN.PK-based, Cas9-expressing strain used for subsequent CRISPR-Cas9-mediated genome modifications (Mans et al., FEMS Yeast Res. 2015 March; 15(2). pii: fov004. doi: 10.1093/femsyr/fov004). IMX774 is a CEN.PK-based strain expressing genes encoding the Calvin cycle enzymes phosphoribulokinase (*S. oleacera* prk) and the single subunit of ribulose-1,5-biphosphate-carboxylase (RuBisCO; *Thiobacillus denitrificans* cbbM), and expressing genes encoding chaperonins (*E. coli* groEL and groES) to aid in the proper folding of the RuBisCO protein in the cytosol of *S. cerevisiae*. The strain construction of IMX774 has been described in European Patent application EP16174382.8 and description is also found below.

TABLE 1

Listing of plasmids used in examples

| Name | Characteristics | Origin |
|---|---|---|
| p426-TEF | 2 μm ori, URA3, empty vector | Mumberg D, et al., Gene, 1995 vol. 156, pp.119-122 |
| pMEL10 | 2 μm ori, URA3, SNR52p-gRNA.CAN1-SUP4t | Mans et al., FEMS Yeast Res. 2015 Mar;15(2). pii: fov004. |
| pMEL11 | 2 μm ori, amdS, SNR52p-gRNA.CAN1-SUP4t | Mans et al., FEMS Yeast Res. 2015 Mar;15(2). pii: fov004. |
| pROS10 | URA3, gRNA. CAN1-2 μm ori-gRNA.ADE2 | Mans et al., FEMS Yeast Res. 2015 Mar;15(2). pii: fov004. |
| pUD232 | Delivery vector, TEF1p-groEL-ACT1t | Guadalupe-Medina et al., Biotechnol Biofuels, 2013, vol. 6, p.125 |
| pUD233 | Delivery vector, TPI1p-groES-PGI1t | Guadalupe-Medina et al., Biotechnol Biofuels, 2013, vol. 6, p.125 |
| pUDE046 | 2 μm ori, GAL1p-prk-CYC1t | Guadalupe-Medina et al., Biotechnol Biofuels, 2013, vol. 6, p.125 |
| pBTWW002 | 2 μm ori, URA3, TDH3p-cbbM-CYC1t | Guadalupe-Medina et al., Biotechnol Biofuels, 2013, vol. 6, p.125 |
| pUDR119 | 2 μm ori, amdS, SNR52p-gRNA.SGA1-SUP4t | EP16174382.8 |
| pUDR164 | 2 μm or URA3, SNR52p-gRNA.X-2-SUP4t | EP16174382.8 |
| pUDR240 | URA3, g RNA. GPD1-2 μm ori-g RNA. GPD2 | EP16174382.8 |
| pDB1332 | Vector with cassette ENO1p-Ec_gldA-CYC1t | Example 1; SEQ ID NO: 1 |
| pDB1333 | Vector with cassette TPI1p-Sc_DAK1-ENO1t | Example 1; SEQ ID NO: 2 |
| pDB1334 | Vector with cassette ADH1p-Dr_T3-TEF2t | Example 1; SEQ ID NO: 3 |
| pDB1336 | Vector with cassette PRE3p-Zr_T5-TEF2t | Example 1: SEQ ID NO 4 |
| pRN1119 | hphMX-bearing shuttle vector based on pRS305 | Example 2; SEQ ID NO: 5 |

CRISPR/Cas9 genome editing was used to perform genetic modifications in IMX581 (resulting in IMX774) according to Mans et al. (2015; FEMS Yeast Res. 2015 March; 15(2). pii: fov004. doi: 10.1093/femsyr/fov004). Unique CRISPR/Cas9 sequences targeting SGA1 or X-2 were identified using a publicly available list (DiCarlo et al., Nucleic Acids Res. 2013; pp. 1-8). For markerless genomic integration of gene cassettes, plasmids expressing unique gRNAs targeting the SGA1 locus or the intergenic region X-2 (Mikkelsen et al., Metabolic Engineering, 2012, volume 14; pp. 101-111) were constructed. The plasmid backbones of pUDR119 and pURD164 were obtained by PCR amplification using the primer combination 5792-5980 and plasmids pMEL11 and pMEL10, respectively, as templates. Phusion® Hot Start II High Fidelity DNA Polymerase (Thermo Scientific, Waltham, Mass., USA) was used for PCR amplification (e.g. for construction of plasmids and expression cassettes) in all cases, according to the manufacturer's guidelines. The plasmid inserts of pUDR119 and pUDR164, containing the expression cassettes coding for the unique 20-bp gRNA sequences targeting SGA1 and X-2 respectively, were obtained by PCR amplification using the primer combinations 5979-7023 for SGA1 and 5979-7374 for X-2 and plasmids pMEL11 and pMEL10, respectively, as templates. The assembly of plasmids pUDR119 and pUDR164 was performed in vitro using the Gibson Assembly® Cloning kit (New England Biolabs, Ipswich, Mass., USA) following the supplier's guidelines. The assembly was enabled by homologous sequences present at the 5' and 3' ends of the PCR-amplified plasmid backbones and inserts. In each case, 1 μl of the Gibson-assembly mix was used for *E. coli* DH5a transformation by electroporation, performed in a Gene PulserXcell Electroporation System (Biorad, Hercules, Calif., USA). Correct assembly of plasmids was confirmed by diagnostic PCR (Dreamtaq®, Thermo Scientific) or restriction digestion. The constructed plasmids pUDR119 and pUDR164 were isolated from transformed *E. coli* cultures using a Sigma GenElute Plasmid kit (Sigma-Aldrich, St. Louis, Mo., USA) and used for transformation of *S. cerevisiae*.

A yeast expression cassette of cbbM was obtained by PCR amplification using plasmid pBTWW002 as template and primer combination 7549-7550. The resulting fragment was ligated to a pJET/1.2 blunt vector (Thermo-Scientific) following the supplier's protocol and cloned to *E. coli*. The resulting plasmid was used as PCR template to generate integration cbbM cassettes, using primer combinations 7074-7075, 7548-6285, 6280-6273, 6281-6270, 6282-6271, 6284-6272, 6283-6275, 6287-6276, 6288-6277, 6289-7075. The expression cassettes of cbbM were genetically identical, except for different overhangs present at the 5' and 3' ends of the fragments to allow for in vivo homologous recombination. Yeast expression cassettes of groEL and groES were obtained using plasmids pUD232 and pUD233 as templates and primer combinations 7076-7077 and 7078-7079, respectively. The genomic sequences corresponding to the DAN1 promoter (Knijnenburg et al., BMC Genomics. 2009; volume 10, p. 53), were obtained by PCR amplification with primer combinations 7930-7931 using genomic DNA of IMX585 as template. The terminator of PGK1 was obtained by PCR amplification with genomic DNA of IMX585 as template using primer combinations 7084-7085 and 7084-7934. The ORF of prk was obtained by PCR amplification using primer combinations 7932-7081 and plasmid pUDE046 as template. The primer combination resulted in prk-ORF fragments with homologous overhangs to the DAN1 promoter sequence and the terminator of PGK1. The complete expression cassette (DAN1p-prk-PGK1t) was assembled by in vivo homologous recombination after transformation to yeast and correct assembly was verified by diagnostic PCR. A complete list of all primers used in the examples is given in Table 2.

transformations performed with plasmid pUDR119, the agar plates were prepared as described previously (Solis-Escalante, FEMS Yeast Res., 2013, volume 13, pp. 126-139). For the construction of strain IMX765 uracil was additionally supplemented to the agar plates (150 mg $L^{-1}$) (Sigma-Aldrich). Confirmation of the desired genotypes in each case was performed by diagnostic colony PCR. Recycling of

TABLE 2

Listing of oligonucleotide primers used in the examples with sequences

| Primer code | SEQ ID | Comment |
|---|---|---|
| 5792 | SEQ ID NO: 17 | pUDR119 and pUDR164 construction |
| 5980 | SEQ ID NO: 18 | pUDR119 and pUDR164 construction |
| 5979 | SEQ ID NO: 19 | pUDR119 and pUDR164 construction |
| 7023 | SEQ ID NO: 20 | pUDR119 construction |
| 7374 | SEQ ID NO: 21 | pUDR164 construction |
| 7549 | SEQ ID NO: 22 | Addition of 20 bp primer-binding sequence to cbbM |
| 7550 | SEQ ID NO: 23 | Addition of 20 bp primer-binding sequence to cbbM |
| 7074 | SEQ ID NO: 24 | cbbM cassette construction-D tag addition (single copy cbbm-prk-chaperone integration) |
| 7075 | SEQ ID NO: 25 | cbbM cassette construction-J tag addition (single copy cbbm-prk-chaperone integration) |
| 7548 | SEQ ID NO: 26 | cbbM cassette construction-SGA1 tag addition |
| 6285 | SEQ ID NO: 27 | cbbM cassette construction-G tag addition |
| 6280 | SEQ ID NO: 28 | cbbM cassette construction-A tag addition |
| 6273 | SEQ ID NO: 29 | cbbM cassette construction-G tag addition |
| 6281 | SEQ ID NO: 30 | cbbM cassette construction-B tag addition |
| 6270 | SEQ ID NO: 31 | cbbM cassette construction-A tag addition |
| 6282 | SEQ ID NO: 32 | cbbM cassette construction-C tag addition |
| 6271 | SEQ ID NO: 33 | cbbM cassette construction-B tag addition |
| 6284 | SEQ ID NO: 34 | cbbM cassette construction-D tag addition |
| 6272 | SEQ ID NO: 35 | cbbM cassette construction-C tag addition |
| 6283 | SEQ ID NO: 36 | cbbM cassette construction-D tag addition |
| 6275 | SEQ ID NO: 37 | cbbM cassette construction-M tag addition |
| 6287 | SEQ ID NO: 38 | cbbM cassette construction-M tag addition |
| 6276 | SEQ ID NO: 39 | cbbM cassette construction-N tag addition |
| 6288 | SEQ ID NO: 40 | cbbM cassette construction-N tag addition |
| 6277 | SEQ ID NO: 41 | cbbM cassette construction-O tag addition |
| 6289 | SEQ ID NO: 42 | cbbM cassette construction-O tag addition |
| 7076 | SEQ ID NO: 43 | groEL cassette construction-J tag addition |
| 7077 | SEQ ID NO: 44 | groEL cassette construction-H tag addition |
| 7078 | SEQ ID NO: 45 | groES cassette construction-H tag addition |
| 7079 | SEQ ID NO: 46 | groES cassette construction-SGA1 tag addition |
| 7930 | SEQ ID NO: 47 | DAN1p prk cassette construction |
| 7931 | SEQ ID NO: 48 | DAN1p prk cassette construction |
| 7084 | SEQ ID NO: 49 | prk cassette construction (PGK1t) |
| 7085 | SEQ ID NO: 50 | prk cassette construction (PGK1t)-D tag addition (single copy cbbm-prk-chaperone integration) |
| 7934 | SEQ ID NO: 51 | prk cassette construction (PGK1t)-X-2 tag addition |
| 7081 | SEQ ID NO: 52 | prk amplification |
| 7932 | SEQ ID NO: 53 | prk amplification (DAN1p cassette) |
| BoZ-783 | SEQ ID NO: 54 | 5'-INT1 amplification |
| BoZ-788 | SEQ ID NO: 55 | 3'-INT1 amplification |
| DBC-13773 | SEQ ID NO: 56 | gRNA-INT1 amplification |
| DBC-13774 | SEQ ID NO: 57 | gRNA-INT1 amplification |
| DBC-13775 | SEQ ID NO: 58 | BB-1119 amplification |
| DBC-13776 | SEQ ID NO: 59 | BB-1119 amplification |
| DBC-14041 | SEQ ID NO: 60 | DAK1 amplification |
| DBC-14042 | SEQ ID NO: 61 | DAK1 amplification |
| DBC-14043 | SEQ ID NO: 62 | gldA amplication |
| DBC-14044 | SEQ ID NO: 63 | gldA amplication |
| DBC-14045 | SEQ ID NO: 64 | T3 amplification |
| DBC-14046 | SEQ ID NO: 65 | T5 amplification |
| DBC-14048 | SEQ ID NO: 66 | T3 amplification |
| DBC-18463 | SEQ ID NO: 67 | 5'-INT1 amplification |
| DBC-18464 | SEQ ID NO: 68 | 3'-INT1 amplification |

The lithium-acetate transformation protocol was used for yeast transformations (Gietz & Woods, Methods Enzymol., 2002, pp. 87-96). Transformation mixtures were plated on Mineral Medium agar plates (Verduyn et al., Yeast, 1992, volume 8, pp. 501-517) (2% Bacto Agar, BD, Franklin Lakes, N.J., USA), supplemented with 20 g $L^{-1}$ glucose in the case of transformations performed with pUDR164. In pUDR164 was performed using 5-fluoro-orotic acid (Zymo Research, Irvine, Calif., USA) counter-selection, following the supplier's guidelines. Recycling of pUDR119 was performed as described previously (Solis-Escalante, FEMS Yeast Res., 2013, volume 13, pp. 126-139). Strain IMX765 was obtained by co-transformation of pUDR119, the 9 abovementioned expression cassettes of cbbM with different connecting overhangs and the expression cassettes of groEL and groES to IMX581 (after plasmid recycling from the correct mutant). Overhangs present at the 5' and 3' ends of the molecules allowed for in vivo assembly of the entire construct (11 fragments) and integration in the SGA1 locus. Strain IMX774 was obtained by transformation of strain IMX765 with the gRNA-expressing, X-2 targeting plasmid pUDR164 and the DAN1p, prk ORF, PGK1t fragments which were assembled in vivo into the complete construct and subsequently integrated in the X-2 locus. The control strain IME324 was obtained by transformation of IMX581 with the empty vector p426-TEF. The genotypes of the strains is indicated in Table 3.

forth referenced as Zr_T5 or T5) under control of S. cerevisiae PRE3 promoter and S. cerevisiae TEF2 terminator.

Example 2: Strain Construction DS78742, DS78743 and DS78744

Approach

The followed strain construction approach is described in patent application PCT/EP2013/056623 and PCT/EP2016/050136. PCT/EP2013/056623 describes the techniques enabling the construction of expression cassettes from various genes of interest in such a way, that these cassettes are

TABLE 3

Listing of S. cerevisiae strains used and generated in the examples.

| Strain name | Relevant Genotype | Origin |
|---|---|---|
| IME324 | MATa ura3-52 can1::cas9-natNT2 + p426-TEF. | EP16174382.8 |
| IMX581 | MATa ura3-52 can1::cas9-natNT2 | Mans et al., FEMS Yeast Res. 2015 Mar;15(2). pii: fov004. |
| IMX585 | MATa can1D::cas9-natNT2 URA3 TRP1 LEU2 HIS3 | Mans et al., FEMS Yeast Res. 2015 Mar;15(2). pii: fov004. |
| IMX765 | MATa ura3-52 can1::cas9-natNT2 sga1::cbbM (9 copies), groES, groEL | EP16174382.8 |
| IMX774 | MATa ura3-52 can1::cas9-natNT2 sga1::cbbM (9 copies), groES, groEL X-2::DAN1p-prk pUDR164 | EP16174382.8 |
| DS78742 | MATa ura3-52 can1::cas9-natNT2 sga1::cbbM (9 copies), groES, groEL X-2::DAN1p-prk pUDR164 int1::TPI1p-DAK1-ENO1t, ENO1p-Ec_gldA-CYC1t, PRE3p-Zr_T5-TEF2t | Example 2 |
| DS78743 | MATa ura3-52 can1::cas9-natNT2 sga1::cbbM (9 copies), groES, groEL X-2::DAN1p-prk pUDR164 int1::TPI1p-DAK1-ENO1t, ENO1p-Ec_gldA-CYC1t, PRE3p-Zr_T5-TEF2t | Example 2 |
| DS78744 | MATa ura3-52 can1::cas9-natNT2 sga1::cbbM (9 copies), groES, groEL X-2::DAN1p-prk pUDR164 int1::TPI1p-DAK1-ENO1t, ENO1p-Ec_gldA-CYC1t, ADH1p-Dr_T3-TEF2t | Example 2 |

Example 1: Glycerol Reuptake Expression Cassette Construction

Expression Cassette Construction

The open reading frames (ORFs), promoter sequences and terminators were synthesized at DNA 2.0 (Menlo Park, Calif. 94025, USA). The promoter, ORF and terminator sequences were recombined by using the Golden Gate technology, as described by Engler et al (2011) and references therein. The expression cassettes were cloned into a standard subcloning vector. The plasmids (listed in Table 1) containing the expression cassettes encoding the components of the glycerol re-uptake pathway are:

pDB1332 (SEQ ID NO: 1) bearing expression cassette for glycerol dehydrogenase (EC 1.1.1.6) E. coli gldA under control of S. cerevisiae ENO1 promoter and S. cerevisiae CYC1 terminator, pDB1333 (SEQ ID NO: 2) bearing expression cassette for dihydroxyacetone kinase (EC 2.7.1.29, EC 2.7.1.28) S. cerevisiae DAK1 under control of S. cerevisiae TPI1 promoter and S. cerevisiae ENO1 terminator, pDB1334 (SEQ ID NO: 3) bearing expression cassette for glycerol transporter/aquaporin D. rerio aqp9 (NP_001171215, hereforth referenced as Dr_T3 or T3) under control of S. cerevisiae ADH1 promoter and S. cerevisiae TEF2 terminator, pDB1336 (SEQ ID NO: 4) bearing expression cassette for glycerol transporter Z. rouxii ZYRO0E01210p (herecombined into a pathway and integrated in a specific locus of the yeast genome upon transformation of this yeast. PCT/EP2016/050136 describes the use of a CRISPR-Cas9 system for integration of expression cassettes into the genome of a host cell, in this case S. cerevisiae. In the construction of IMX774 a S. pyogenes Cas9 expression cassette was already integrated at the CAN1 locus. Upon introduction of an in vivo assembled gRNA-expressing plasmid and repair DNA fragments the intended modifications were made. Firstly, an integration site in the yeast genome was selected. DNA fragments of approximately 500 bp of the up- and downstream parts of the integration locus were amplified by PCR using primers introducing connectors to the generated PCR products. These connectors (50 bp in size) allow for correct in vivo recombination of the pathway upon transformation in yeast. Secondly, the genes of interest, are amplified by PCR, incorporating a different connector (compatible with the connector on the of the neighbouring biobrick) at each flank. Upon transformation of yeast cells with the DNA fragments, in vivo recombination and integration into the genome takes place at the desired location. This technique facilitates parallel testing of multiple genetic designs, as one or more genes from the pathway can be replaced with (an)other gene(s) or genetic element(s), as long as that the connectors that allow for homologous recombination remain constant and compatible with the preceeding and following biobrick in the design (patent application PCT/EP2013/056623).

gRNA Expression Plasmid

Integration site: the expression cassettes were targeted at the INT1 locus. The INT1 integration site is a non-coding region between NTR1 (YOR071c) and GYP1 (YOR070c) located on chromosome XV of *S. cerevisiae*. The guide sequence to target INT1 was designed with a gRNA designer tool (dna20.com/eCommerce/cas9/input).

The gRNA expression cassette (as described by DiCarlo et al., Nucleic Acids Res. 2013; pp. 1-8) was ordered as synthetic DNA cassette (gBLOCK) at Integrated DNA Technologies (Leuven, Belgium) (INT1 gBLOCK; SEQ ID NO: 6). In vivo assembly of the gRNA expression plasmid is then completed by co-transforming a linear fragment derived from yeast vector pRN1119. pRN11119 is a multi-copy yeast shuttling vector that contains a functional hphMX marker cassette conferring resistance against Hygromycin B (HygB). The backbone of this plasmid is based on pRS305 (Sikorski and Hieter, Genetics 1989, vol. 122, pp. 19-27), including a functional 2 micron ORI sequence and a functional hphMX marker cassette (SEQ ID NO: 5, Table 1).

Transformation of IMX774 with Specified DNA Fragments Upon Assembly Comprising Glycerol Reuptake Pathway Designs Strain IMX774 was transformed with the following fragments resulting the assembly of the glycerol reuptake pathway as depicted in FIG. 1:

1) a PCR fragment (5'-INT1) generated with primers BoZ-783 and DBC-18463 with genomic DNA of strain CEN.PK113-7D as template;
2) a PCR fragment (DAK1) generated with primers DBC-14041 and DBC-14042 using pDB1333 (SEQ ID NO: 1) as template;
3) a PCR fragment (gldA) generated with primers DBC-14043 and DBC-DBC-14044 using pDB1332 (SEQ ID NO: 2) as template;
4) a PCR fragment (T3) generated with primers DBC-14045 and DBC-14048 using pDB1334 (SEQ ID NO: 3) as template; or a PCR fragment (T5) generated with primers DBC-14046 and DBC-14048 using pDB1336 (SEQ ID NO: 4) as template;
5) a PCR fragment (3'-INT1) generated with primers DBC-18464 and BoZ-788 using genomic DNA of strain CEN.PK113-7D as template;
6) a PCR fragment (BB-1119) generated with primers DBC-13775 and DBC-13776 using pRN1119 (SEQ ID NO: 5) as template;
7) a PCR fragment (gRNA-INT1) generated with primers DBC-13773 and DBC-13774 using INT1 gRNA (SEQ ID NO: 6) as template;

Transformants were selected on YEPh-agar plates containing 20 g/L glucose and 200 µg HygB/ml. Diagnostic PCR was performed to confirm the correct assembly and integration at the INT1 locus of the pathway with T5 in strains DS78742 and DS78743 and with T3 in DS78744 (see Table 3 for genotypes).

Example 3: Fermentation Experiment

Propagation of Strains

Strains IME324, IMX774, DS78742, DS784743 and DS78744 were pre-grown at 30° C. and 280 rpm overnight under semi-aerobic conditions in Mineral Medium supplemented with 20 g/L glucose supplemented with 0.05 g/L uracil.

Preparation of AFM Experiment

The following day, the optical density at 600 nm was determined and cells were spun down by centrifugation. Four hundred ml of Mineral Medium containing approximately 50 grams of glucose per liter and 0.05 g/L uracil was inoculated with one the abovementioned strains to 0.075 g/L (dry weight). At specific time intervals samples were taken in order to measure biomass, residual sugars, glycerol and acetic acid, as well as the formation of ethanol.

Results Fermentation Experiment

Figure 2:
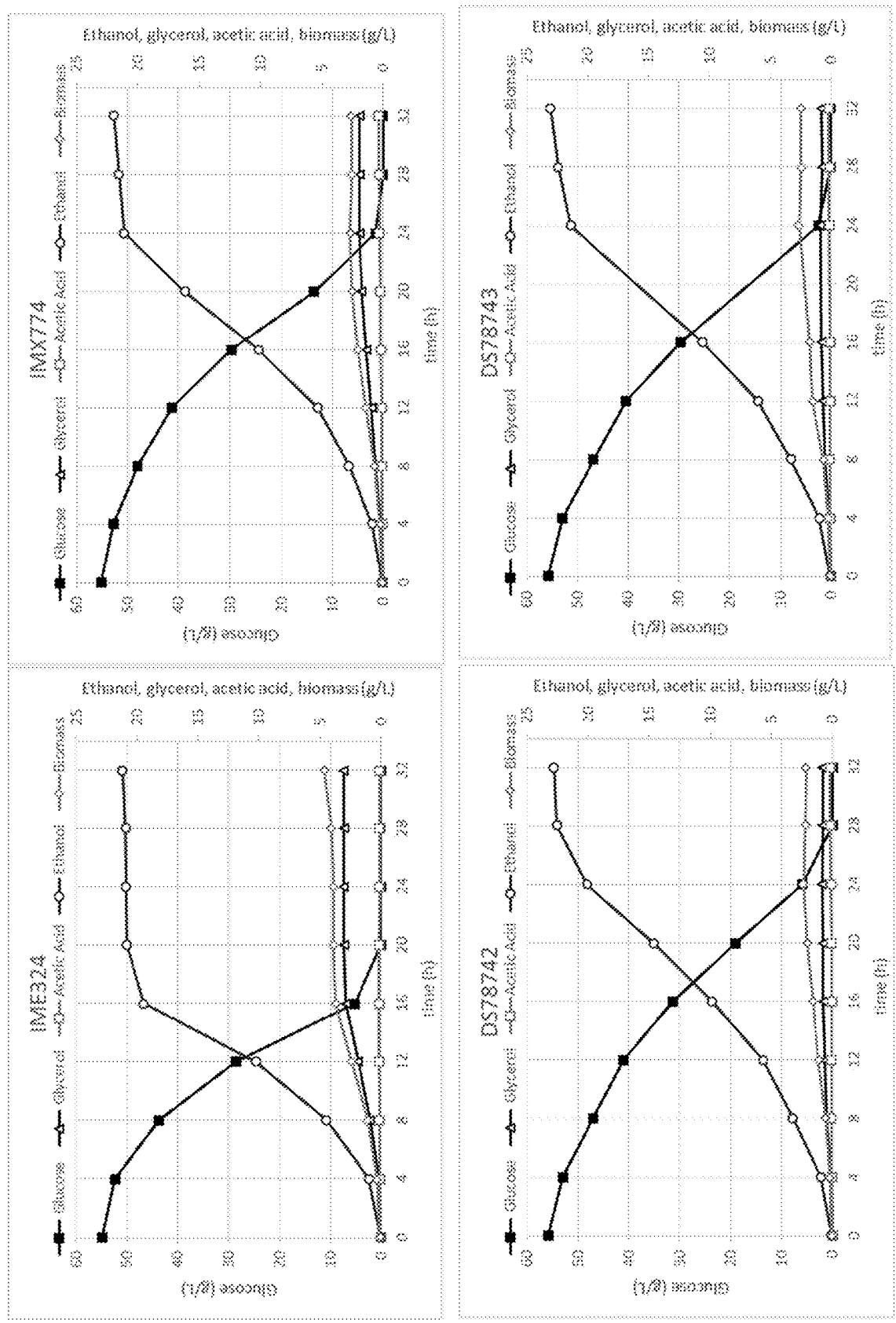
FIG. 2: Fermentation profiles of strains IME324, IMX774, DS78742, DS78743, DS787444 on a mineral medium supplemented with approximately 50 g glucose per liter; initial pH of medium was 4.6. Levels of residual glucose (g/L; solid squares, black line) and formed biomass (g/L; open diamonds, grey line), glycerol (g/L; open triangles, black line), acetic acid (g/L; open squares, grey line) and ethanol (g/L; open circles, black line) were measured every 4 hours during a 32 h fermentation run.
Figure 2:
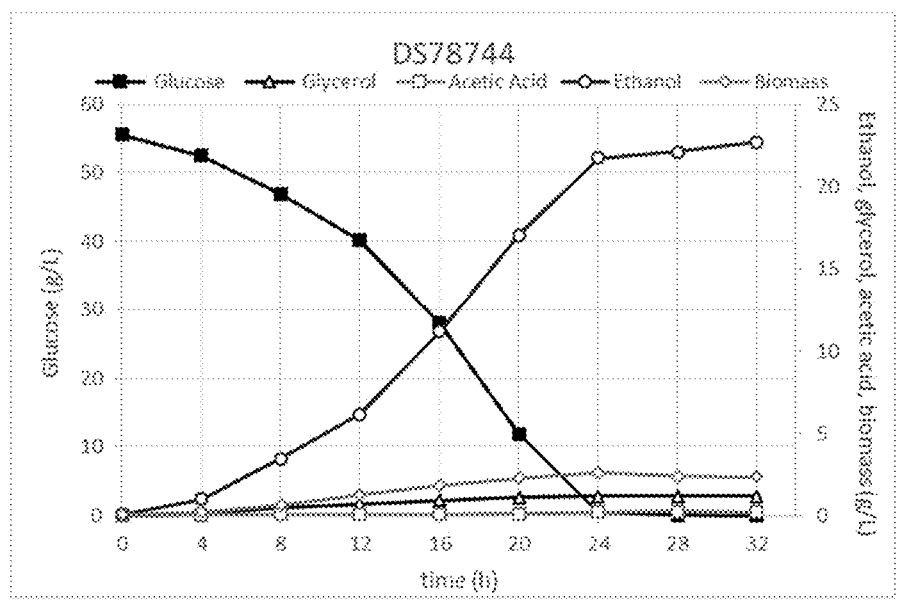

The glycerol yield on glucose of strains IMX774, DS78742, DS78743 and DS78744 were 0.036, 0.014, 0.015. and 0.021 g/g, respectively, which corresponds to a 35%, 75%, 73% and 62%, respectively, decrease compared to the reference strain IME324 (Table 4, FIG. 2). A decrease of glycerol production can be expected when $NAD^+$ is, at least partly, regenerated via the RuBisCO pathway. The glycerol that is produced by the strain, since the Gpd1/Gpd2/Gpp1/Gpp2 pathway is left intact, and possibly already secreted by the cell is taken up again by either the T5 or T3 glycerol transporters and re-shuttled to glycolysis, and, subsequently, ethanol fermentation, by the concerted action of gldA and DAK1. The re-shuttling of glycerol to ethanol comes at the cost of 1 ATP and yields one NADH per mole of glycerol that is available for re-oxidation via the Prk-RuBisCO pathway, thereby increasing the flux through this pathway further, and effectively decreasing the net glycerol produced in fermentation. As a combined result of the decrease in glycerol production, $CO_2$ fixation via the Prk-RuBisCO pathway, and a decrease in biomass yield, the engineered, RuBisCO expressing strain IMX774 produced 3% more ethanol compared to the reference strain. Even more, the additional re-shuttling of formed glycerol through the glycerol-reuptake pathway (T5/T3-gldA-DAK1) (Table 4, FIG. 2) by strains DS78742, DS78743 and DS78744 resulted in a further increase towards ca. 6%, 7% and 5%, respectively, in ethanol yield compared to the reference strain on ca. 50 g/L glucose in the experiments performed in this example.

TABLE 4

Fermentation yields and growth characteristics of strains IME324, IMX774, DS78742, DS78743 and DS78744 on Mineral Medium supplemented with ca. 50 g/L glucose.

| Strain Relevant genotype | IME324 reference | IMX774 9*cbbM, DAN1p-prk, groES, groEL | DS78742 9*cbbM, DAN1p-prk, groES, groEL, gldA, DAK1, T5 | DS78743 9*cbbM, DAN1p-prk, groES, groEL, gldA, DAK1, T5 | DS78744 9*cbbM, DAN1p-prk, groES, groEL, gldA, DAK1, T3 |
|---|---|---|---|---|---|
| Y glycerol/glucose (g/g) | 0.056 | 0.036 | 0.014 | 0.015 | 0.021 |
| Y biomass/glucose (g/g$^{-1}$) | 0.085 | 0.048 | 0.040 | 0.045 | 0.042 |

TABLE 4-continued

Fermentation yields and growth characteristics of strains IME324, IMX774, DS78742, DS78743 and DS78744 on Mineral Medium supplemented with ca. 50 g/L glucose.

| Strain Relevant genotype | IME324 reference | IMX774 9*cbbM, DAN1p-prk, groES, groEL | DS78742 9*cbbM, DAN1p-prk, groES, groEL, gldA, DAK1, T5 | DS78743 9*cbbM, DAN1p-prk, groES, groEL, gldA, DAK1, T5 | DS78744 9*cbbM, DAN1p-prk, groES, groEL, gldA, DAK1, T3 |
|---|---|---|---|---|---|
| Y EtOH/glucose (g/g) | 0.387 | 0.398 | 0.409 | 0.414 | 0.408 |
| Ratio glycerol produced/ biomass (mmol/$g_x$) | 7.2 | 8.3 | 3.9 | 3.5 | 5.5 |

The invention claimed is:

1. A recombinant cell comprising:
a) one or more heterologous genes encoding a glycerol dehydrogenase;
b) one or more genes encoding a dihydroxyacetone kinase (E.C. 2.7.1.28 and/or E.C. 2.7.1.29);
c) one or more heterologous genes encoding a ribulose-1,5-biphosphate carboxylase oxygenase (EC 4.1.1.39, RuBisCO); and
d) one or more heterologous genes encoding a phosphoribulokinase (EC 2.7.1.19, PRK); and optionally
e) one or more heterologous genes encoding a glycerol transporter, wherein the recombinant cell comprises overexpression of one or more pentose phosphate pathway (PPP)-genes.

2. The cell according to claim 1, wherein the cell comprises overexpression of one or more of TAL1, TAL2, TKL1, TKL2, RPE1 and RKI1.

3. The cell according to claim 1, wherein the cell comprises overexpression of TKL1.

4. The cell according to claim 1 which comprises a deletion or disruption of one or more endogenous nucleotide sequences encoding a glycerol exporter.

5. The cell according to claim 1 wherein the glycerol dehydrogenase is a NAD+ linked glycerol dehydrogenase (EC 1.1.1.6) or a NADP+ linked glycerol dehydrogenase (EC 1.1.1.72).

6. The cell according to claim 1 which comprises a genetic modification that increases the specific activity of dihydroxyacetone kinase in the cell as compared to a cell which is genetically identical except for the modification causing the increased specific activity of dihydroxyacetone kinase.

7. The cell according to claim 1 which comprises a deletion or disruption of one or more endogenous nucleotide sequences encoding a glycerol kinase (EC 2.7.1.30).

8. The cell according to claim 1 which comprises a deletion or disruption of one or more endogenous nucleotide sequences encoding a glycerol-3-phosphate dehydrogenase, which glycerol-3-phosphate dehydrogenase optionally belongs to EC 1.1.5.3, optionally gut2, or to EC 1.1.1.8, optionally PDP 1/2, which cell is optionally free of genes encoding NADH-dependent glycerol 3-phosphate dehydrogenase.

9. The cell according to claim 1 which comprises a deletion or disruption of one or more endogenous nucleotide sequences encoding a glycerol 3-phosphate phosphohydrolase (GPP 1/2).

10. The cell according to claim 1 which comprises one or more nucleic acid sequences encoding a heterologous glycerol transporter represented by amino acid sequence SEQ ID NO: 7 or a functional homologue thereof having sequence identity of at least 50%.

11. The cell according to claim 1 which comprises one or more nucleic acid sequences encoding a heterologous glycerol transporter represented by amino acid sequence SEQ ID NO: 8 or a functional homologue thereof having sequence identity of at least 50%.

12. The cell according to claim 1 which is a yeast cell.

13. The cell according to claim 1 which is selected from Saccharomycetaceae, optionally from the group of *Saccharomyces*, optionally *Saccharomyces cerevisiae*; *Kluyveromyces*, optionally *Kluyveromyces marxianus*; *Pichia*, optionally *Pichia stipitis* or *Pichia angusta*; *Zygosaccharomyces*, optionally *Zygosaccharomyces bailit*; and *Brettanomyces*, optionally *Brettanomyces intermedius, Issatchenkia*, optionally *Issatchenkia orientalis* and *Hansenula*.

14. The cell according to claim 1 further comprising one or more genes, optionally a heterologous genes, encoding molecular chaperones, said chaperones optionally originating from a prokaryote, optionally a bacterium, optionally *E. coli*, optionally said chaperones are selected from the group consisting of GroEL, GroES, functional homologues of GroEL, and functional homologues of GroES.

15. The cell according to claim 1 wherein the PRK is under control of a promoter that enables higher expression under anaerobic conditions than under aerobic conditions, with a PRK expression ratio anaerobic/aerobic of 2 or more, 3 or more, 4 or more, 5 or more, 6 or more, 7 or more, 8 or more, 9 or more, 10 or more, 20 or more or 50 or more.

16. A process for preparing a fermentation product, comprising preparing a fermentation product from a fermentable carbohydrate, optionally selected from the group of glucose, fructose, sucrose, maltose, xylose, arabinose, galactose and mannose, wherein said preparing is carried out by contacting the cell according to claim 1 with the fermentable carbohydrate under anaerobic conditions.

17. The process according to claim 16 wherein the fermentable carbohydrate is obtained from starch, lignocellulose, and/or pectin.

18. The process according to claim 17, wherein the starch, lignocellulose, and/or pectin is contacted with an enzyme composition, wherein one or more sugar is produced, and wherein the produced sugar is fermented to give a fermentation product, wherein the fermentation is conducted with said cell.

19. The process according to claim 16, wherein the fermentation product is one or more of ethanol, butanol, lactic acid, succinic acid, a plastic, an organic acid, a solvent, an animal feed supplement, a pharmaceutical, a vitamin, an amino acid, an enzyme or a chemical feedstock.

20. The cell according to claim 15, wherein the promoter is a PRK promoter.

* * * * *